(12) United States Patent
Gunura et al.

(10) Patent No.: US 11,013,333 B2
(45) Date of Patent: May 25, 2021

(54) WEARABLE SITTING POSTURE ASSISTING DEVICE

(71) Applicant: noonee AG, Zurich (CH)

(72) Inventors: Keith Gunura, Zurich (CH); Daniel Vafi, Zurich (CH); Robin Jergen, Adliswil (CH); Simon Hutter, Au (CH); Willy Huwyler, Cham (CH)

(73) Assignee: noonee AG, Zurich (CH)

( * ) Notice: Subject to any disclaimer, the term of this patent is extended or adjusted under 35 U.S.C. 154(b) by 0 days.

(21) Appl. No.: 16/346,162

(22) PCT Filed: Nov. 8, 2017

(86) PCT No.: PCT/EP2017/078664
§ 371 (c)(1),
(2) Date: Apr. 30, 2019

(87) PCT Pub. No.: WO2018/087180
PCT Pub. Date: May 17, 2018

(65) Prior Publication Data
US 2020/0046132 A1  Feb. 13, 2020

(30) Foreign Application Priority Data
Nov. 8, 2016  (EP) .................................. 16197787

(51) Int. Cl.
*A47C 9/10* (2006.01)
*F16C 1/10* (2006.01)

(52) U.S. Cl.
CPC ................ *A47C 9/10* (2013.01); *F16C 1/106* (2013.01)

(58) Field of Classification Search
CPC .................................. A47C 9/10; F16C 1/106
USPC ............................................................. 297/4
See application file for complete search history.

(56) References Cited

U.S. PATENT DOCUMENTS

| | | | |
|---|---|---|---|
| 3,538,512 A | | 11/1970 | Dolan |
| 4,697,808 A | * | 10/1987 | Larson .................. A61F 5/0102 482/4 |
| 5,888,215 A | * | 3/1999 | Roos .................. A61B 17/8605 623/33 |

(Continued)

FOREIGN PATENT DOCUMENTS

| | | |
|---|---|---|
| CN | 104970579 A | 10/2015 |
| EP | 1 637 114 A1 | 3/2006 |

(Continued)

OTHER PUBLICATIONS

Partial European Search Report dated May 9, 2017 issued in corresponding EP patent application No. 16197787.1.
Extended European Search Report dated Jul. 31, 2017 issued in corresponding EP patent application No. 16197787.1.

(Continued)

*Primary Examiner* — Mark R Wendell
(74) *Attorney, Agent, or Firm* — Posz Law Group, PLC

(57) ABSTRACT

A wearable sitting posture assisting device includes at least one leg unit featuring at least one knee joint and featuring at least one locking unit for the knee joint; includes at least one second leg unit featuring at least one second knee joint and featuring at least one second locking unit; and includes at least one actuation unit featuring at least one manually operable actuation element for mechanically controlling the locking unit and/or the second locking unit.

16 Claims, 11 Drawing Sheets

(56) References Cited

U.S. PATENT DOCUMENTS

Figure 1:
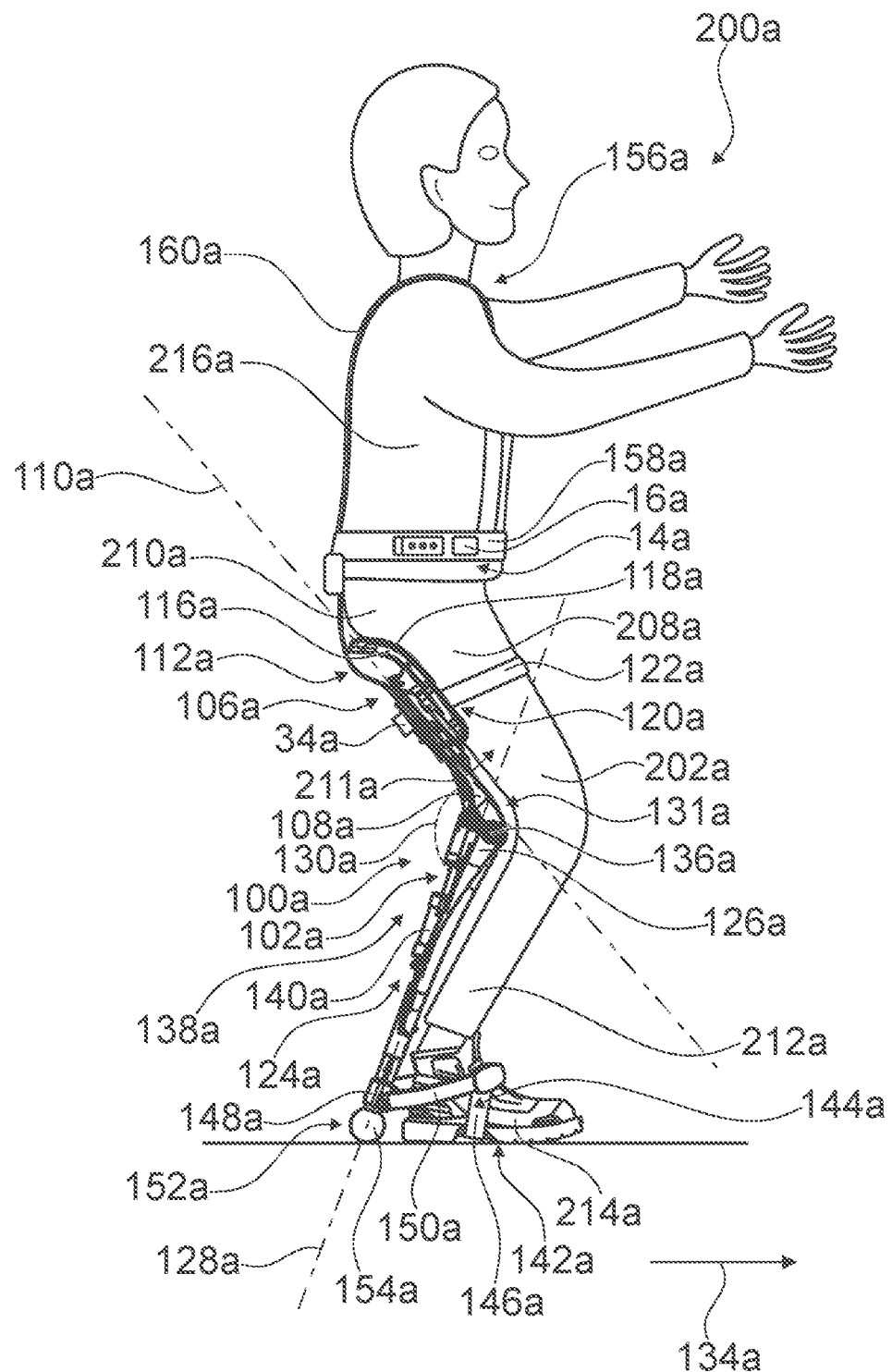

| | | | | |
|---|---|---|---|---|
| 6,263,892 | B1* | 7/2001 | Baker | A61H 3/02 135/66 |
| 10,271,660 | B2* | 4/2019 | Gunura | A47C 9/025 |
| 10,537,459 | B2* | 1/2020 | Gunura | A61F 5/0125 |
| 2009/0198162 | A1 | 8/2009 | DeHarde et al. | |
| 2009/0312844 | A1* | 12/2009 | Ikeuchi | A61H 3/008 623/40 |
| 2013/0197408 | A1 | 8/2013 | Goldfarb et al. | |
| 2016/0135604 | A1* | 5/2016 | Kim | A47C 4/04 297/4 |
| 2016/0175180 | A1* | 6/2016 | Bond | A61F 5/0102 602/23 |
| 2016/0317340 | A1* | 11/2016 | Jangir | A41F 9/00 |
| 2016/0331486 | A1* | 11/2016 | Nakatani | B25J 9/0006 |

FOREIGN PATENT DOCUMENTS

| | | |
|---|---|---|
| EP | 3 095 428 A1 | 11/2016 |
| JP | 3141172 U | 4/2008 |
| WO | 2015/028373 A1 | 3/2015 |
| WO | 2015/107576 A1 | 7/2015 |

OTHER PUBLICATIONS

International Search Report and Written Opinion of the International Searching Authority dated May 30, 2018 issued in corresponding International patent application No. PCT/EP2017/078664.
International Preliminary Report on Patentability dated May 14, 2019 issued in corresponding International patent application No. PCT/EP2017/078664.

* cited by examiner

WEARABLE SITTING POSTURE ASSISTING DEVICE

CROSS REFERENCE TO RELATED APPLICATIONS

This application is a U.S. national stage application of PCT/EP2017/078664 filed on Nov. 8, 2017, which is based on European Patent Application No. 16197787.1 filed on Nov. 8, 2016, the contents of which are incorporated herein by reference.

STATE OF THE ART

The invention relates to a wearable sitting posture assisting device.

A posture assisting device is known from the document WO 2015/028373 A1.

The objective of the invention is, in particular, to provide a generic wearable sitting posture assisting device with improved characteristics regarding comfort. The objective is achieved according to the invention by the features the independent claims, while advantageous embodiments and further developments of the invention may be gathered from the dependent claims.

Advantages of the Invention

A wearable sitting posture assisting device is proposed, comprising at least one leg unit featuring at least one knee joint and featuring at least one locking unit for the knee joint; comprising at least one second leg unit featuring at least one second knee joint and featuring at least one second locking unit; and comprising at least one actuation unit featuring at least one manually operable actuation element for mechanically controlling the locking unit and/or the second locking unit.

By means of the invention a high degree of comfort can be achieved. A wearable sitting posture assisting device featuring improved characteristics concerning user-friendliness and/or wearing comfort can be provided. Furthermore, a high degree of reliability can be achieved. In addition, an intuitive handling can be achieved. A locking mechanism for a wearable sitting posture assisting device, which is easy to handle and/or reliable can be provided. In addition, a user is enabled to use a wearable sitting posture assisting device in a flexible manner and/or in a manner adjusted to his wishes and/or requirements. Advantageously, a locking mechanism can be provided which helps preventing operating errors. Furthermore, a wearable sitting posture assisting device can be provided which is easy to put on or off. Advantageously, a comfortable and/or reliable wearable sitting posture assisting device for use in a factory building and/or at an assembly line and/or in an office building and/or in a service building and/or in a domestic building or the like can be provided.

A "wearable sitting posture assisting device" is herein to be understood as a device which is configured for receiving a weight force of a person in a sitting posture or in a partly sitting posture and to transmit the weight force to a ground. In particular, an angle between a thigh and a shank of the person in the sitting posture is no greater than 130°, preferably no greater than 120° and advantageously no greater than 110° and/or no smaller than 60°, preferably no smaller than 70° and advantageously no smaller than 80°. In particular, the angle between the thigh and the shank of the person is approximately 90° in the sitting posture. In particular, an angle between a thigh and a shank of the person in the partly sitting posture is no greater than 170°, preferably no greater than 160° and advantageously no greater than 150° and/or no smaller than 100°, preferably no smaller than 110° and advantageously no smaller than 120°. In particular, the angle between the thigh and the shank of the person is approximately 130° in the partly sitting posture. It is conceivable that the partly sitting posture is a posture in which the person is leaning forward while partly bending his knees. In particular, a person wearing the wearable sitting posture assisting device is enabled to sit and/or to partly sit and/or to take a seat on the wearable sitting posture assisting device, wherein at least a part of the weight force is counteracted by the wearable sitting posture assisting device and/or wherein the person is counteracting only a fraction of the weight force using his muscles. In particular, the wearable sitting posture assisting device is configured for being worn by the person while the person is standing and/or while the person is walking. Advantageously, the wearable sitting posture assisting device is configured for supporting different sitting postures and/or partly sitting postures, which are in particular characterized by different sitting angles.

The wearable sitting posture assisting device in particular defines a sitting direction. Preferably, the person faces and/or looks in the sitting direction when sitting or partly sitting on the wearable sitting posture assisting device and facing forward. In particular, the sitting direction is oriented parallel to a floor on which the person is standing and/or sitting and/or walking when wearing the wearable sitting posture assisting device. In particular, the wearable sitting posture assisting device defines a walking direction. Preferably, the person faces in the walking direction when walking and/or standing with the wearable sitting posture assisting device and facing forward. In particular, the walking direction is oriented parallel to a floor on which the person is standing and/or sitting and/or walking when wearing the wearable sitting posture assisting device. In particular, the wearable sitting posture assisting device is only designed to receive and transmit the weight force. Preferably, the wearable sitting posture assisting device is not designed to generate a controllable force, which is provided to assist a person while walking, standing or lifting some loads. In this context, "configured" is in particular to mean specifically programmed, designed and/or equipped. By an object being configured for a certain function is in particular to be understood that the object implements and/or fulfills said certain function in at least one application state and/or operating state.

Preferably, the wearable sitting posture assisting device comprises at least one leg unit. In particular, the wearable sitting posture assisting device comprises at least one second leg unit. In particular, the leg unit comprises at least one, preferably one, upper leg and/or at least one, preferably one, lower leg and/or at least one, preferably one, foot unit and/or at least one, preferably one, ground contact unit. Advantageously, the upper leg is connected to the lower leg, in particular via at least one, in particular one, knee joint. Preferably, the foot unit is connected to the lower leg. Advantageously, the ground contact unit is connected to the lower leg and/or to the foot unit. It is conceivable that the ground contact unit is at least partly implemented integrally with the lower leg and/or at least partly implemented integrally with the foot unit. It is also conceivable that the foot unit is at least partly implemented integrally with the lower leg. Preferably, the wearable sitting posture assisting device comprises at least one upper body wearing unit. In particular, the leg unit is connected to the upper body wearing unit, preferably via at least one connection strap. In this context, the term "a first object and a second object being at least partly implemented integrally" is in particular to mean that at least one component of the first object and at least one component of the second object are implemented integrally with each other. "Implemented integrally" is in particular to mean, in this context, connected at least by substance-to-substance bond, e.g., by a welding process, an adhesive bonding, an injection-molding process and/or by another process that is deemed expedient by a person having ordinary skill in the art. Advantageously, "implemented integrally" could in particular mean made of one piece. "Made of one piece" is, in particular, to mean, in this context, manufactured from one single piece, e.g., by production from one single cast and/or by manufacturing in a one-component or multi-component injection-molding process, and advantageously from a single blank.

Preferably, the wearable sitting posture assisting device comprises two leg units. Advantageously, the leg unit and the second leg unit are implemented identically. It is also conceivable that the leg unit and the second leg unit are implemented mirror-symmetrically with respect to each other. It is conceivable that the leg unit is configured for being worn on a left leg and the second leg unit is configured for being worn at a right leg, or vice versa. Advantageously, the leg unit is configured for being worn either on a left leg or on a right leg. Further advantageously, the second leg unit is configured for being worn on a left leg or on a right leg. Preferably, the second leg unit is connected to the upper body wearing unit, preferably via at least one connection strap. In particular, the person wearing the wearable sitting posture assisting device is wearing the leg unit, in particular solely, on a first leg, for instance a left leg or a right leg. In particular, the person wearing the wearable sitting posture assisting device is wearing the second leg unit, in particular solely, on a second leg, for instance a right leg or a left leg. Advantageously, the leg unit is arranged on a rear side of the leg on which the leg unit is worn. Further advantageously, the second leg unit is arranged on a read side of the leg on which the second leg unit is worn. In particular, the leg units of the wearable sitting posture assisting device are arranged on a rear side of the legs of the person when the person is sitting and/or partly sitting on the wearable sitting posture assisting device and/or standing and/or walking with the wearable sitting posture assisting device. Preferably, the person wearing the wearable sitting posture assisting device is wearing the upper body wearing unit on his upper body. Advantageously, the upper body wearing unit is implemented as a belt and/or as braces and/or as suspenders. The wearable sitting posture assisting device enables the person wearing it to walk around, stand, take a seat on the wearable sitting posture assisting device if required or wanted and stand up after sitting or partly sitting on the wearable sitting posture assisting device.

Preferably, the upper leg comprises at least one thigh connection unit for connecting to a thigh of the person. Preferably, the thigh connection unit features at least one thigh strap. In particular, the upper leg comprises a seat unit configured for providing at least one sitting surface for the person, in particular in case the person is sitting or partly sitting on the wearable sitting posture assisting device, preferably for the thigh and/or at least a lower portion of a buttock of the person, wherein "buttock" is preferably to mean one cheek of the buttocks. Preferably, the seat unit comprises at least one sitting element which features the sitting surface. Advantageously, the seat unit is in contact with the thigh of the person in case the person is sitting or partly sitting on the wearable sitting posture assisting device. Preferably, the seat unit is arranged on a rear side of the thigh of the person in case the person is standing or walking with the wearable sitting posture assisting device.

Advantageously, the upper leg comprises at least one upper leg support. Preferably, the seat unit is connected to the upper leg support. Advantageously, the thigh connection unit and/or the thigh strap is connected to the upper leg support. In particular, the upper leg support is implemented as a frame element. Preferably, the upper leg support is implemented as an elongated element. Advantageously, the upper leg features at least one upper leg longitudinal axis which is oriented at least substantially parallel to a longitudinal axis of the thigh of the person. Preferably, a main extension direction of the upper leg support is oriented at least substantially parallel, or parallel, to the upper leg longitudinal axis. In particular, the upper leg support is at least partly, preferably at least to a large extent, advantageously completely made of plastic. It is also conceivable that the upper leg support is at least partly, preferably at least to a large extent, advantageously completely made of metal, in particular made of a light metal or a light alloy, for instance aluminum and/or titanium and/or beryllium and/or scandium or other suitable metals. It is further conceivable that the upper leg support is at least partly, preferably at least to a large extent, advantageously completely made of a composite material, in particular a fiber reinforced composite material and/or a fiber reinforced plastic and/or a carbon fiber reinforced material and/or a carbon fiber reinforced polymer and/or a fiber reinforced thermoplastic. The term "at least to a large extent" is in particular to mean to an extent of at least 55%, preferably to an extent of at least 65%, further preferably to an extent of at least 75%, advantageously to an extent of at least 85% and further advantageously to an extent of at least 95%. In this context "at least substantially parallel" is in particular to be understood as an orientation of a direction with respect to a reference direction, in particular in a plane, wherein the direction has a deviation from the reference direction in particular of less than 15°, advantageously of less than 10° and particularly advantageously of less than 2°. A "main extension direction" of an object is, in particular, to be understood, in this context, as a direction extending in parallel to a largest side of an imaginary rectangular cuboid which only just entirely encloses the object.

Preferably, the lower leg is arranged at a rear side of the shank of the person. In particular, the lower leg comprises at least one lower leg support. Advantageously, the lower leg support is implemented as a frame element. Preferably, the lower leg support is implemented as an elongated element. In particular, the lower leg features at least one lower leg longitudinal axis which is oriented at least substantially parallel to a longitudinal axis of the shank of the person. Preferably, a main extension direction of the lower leg support is oriented at least substantially parallel, or parallel, to the lower leg longitudinal axis. Advantageously, the lower leg longitudinal axis is oriented at least substantially parallel, or parallel, to the upper leg longitudinal axis.

Preferably, the upper leg and the lower leg together define a sitting angle. Advantageously, the sitting angle is an angle included between the upper leg longitudinal axis and the lower leg longitudinal axis, in particular on a rear side of the upper leg and the lower leg. In particular, in the sitting posture the sitting angle is no greater than 130°, preferably no greater than 120° and advantageously no greater than 110° and/or no smaller than 60°, preferably no smaller than 70° and advantageously no smaller than 80°. In particular, the sitting angle is approximately 90° in the sitting posture.

In particular, in the partly sitting posture the sitting angle is no greater than 170°, preferably no greater than 160° and advantageously no greater than 150° and/or no smaller than 100°, preferably no smaller than 110° and advantageously no smaller than 120°. In particular, the sitting angle is approximately 130° in the partly sitting posture. Preferably, the sitting angle equals the angle between the thigh and the shank of the person. In particular, the sitting angle is approximately 180° in a standing posture.

In particular, the knee joint is pivotably connecting the lower leg to the upper leg, preferably pivotably about a knee joint axis. Advantageously, the knee joint axis is oriented at least substantially perpendicularly, or perpendicularly, to the upper leg longitudinal axis and/or to the lower leg longitudinal axis. Preferably, the knee joint axis is oriented at least substantially perpendicularly, or perpendicularly, to the sitting direction. Advantageously, the upper leg support and the lower leg support together implement at least a portion of the knee joint, or the knee joint. Preferably, a value of the sitting angle corresponds to a value of a knee joint position of the knee joint. In this context "at least substantially perpendicular" is in particular to be understood as an orientation of a direction with respect to a reference direction, in particular in a plane, wherein the direction and the reference direction include an angle, which angle deviates from an angle of 90° by no more than 15°, advantageously by no more than 10° and particularly advantageously by no more than 2°.

Preferably, the wearable sitting posture assisting device comprises at least one locking unit, which is configured for locking the upper leg with respect to the lower leg and/or the knee joint in a certain sitting angle and/or is configured for defining a smallest sitting angle. Advantageously, the locking unit is configured for locking the knee joint in different sitting angles, and/or for defining different smallest sitting angles, which sitting angles can be preferably chosen by the person. It is conceivable that the locking unit is configured for allowing to increase the sitting angle in a locked state. In particular, the person is enabled to stand up when the locking unit is in the locked state. Preferably, the locking unit is configured for enabling the person to sit down again at the defined smallest sitting angle after standing up with the locking unit still defining the same smallest sitting angle. Advantageously, the locking unit comprises at least one blocking element which is configured for blocking and/or unblocking the knee joint and/or for locking the sitting angle and/or for defining a smallest sitting angle. Preferably, the blocking element is implemented as a spring, in particular as a gas spring. Advantageously, the blocking element is connected to the upper leg, in particular to the upper leg support, and to the lower leg, in particular to the lower leg support. Preferably, the blocking element is configured for damping a movement of the upper leg with respect to the lower leg during sitting down and/or during standing up. In particular, the foot unit is configured for connecting to a shoe and/or to a foot of the person and/or the foot unit is connected to a shoe and/or to a foot of the person. Preferably, the foot unit comprises at least one shoe connector for connecting to the foot and/or to the shoe of the person. Advantageously, the foot connector features at least one shoe strap. In particular, the foot connector features at least one upper strap, which advantageously runs across an instep of the foot or of the shoe the foot unit is connected to. Preferably, the foot connector features at least one lower strap, which advantageously runs across a sole of the foot or of the shoe the foot unit connected to. Preferably, the foot connector is configured for being worn on a shoe and/or on a foot. Advantageously, the foot unit comprises at least one foot unit support. Preferably, the shoe connector is connected to the foot unit support. Advantageously, the foot unit support comprises at least one bracket and/or the foot unit support element is implemented as a bracket. Preferably, the shoe strap, in particular the upper strap and/or the lower strap, is connected to the bracket. It is conceivable that the foot unit support element is at least partly implemented integrally, or implemented integrally, with the lower leg, in particular with the lower leg support.

In particular, the ground contact unit comprises at least one ground contact element. Preferably, the ground contact element features at least one ground contact surface, which is advantageously configured for contacting a ground when the person is sitting or partly sitting on the wearable sitting posture assisting device. Advantageously, the ground contact surface is bent and/or curved, in particular convexly bent and/or convexly curved. Preferably, at least a portion of the ground contact element or the entire ground contact element is ellipsoidally and/or spheroidally and/or spherically shaped. In particular, the ground contact element is at least partly, preferably at least to a large extent, advantageously completely made of rubber. Preferably, a weight force of the person is transmitted from the seat unit to the upper leg support and/or from the upper leg support to the knee joint and/or from the knee joint to the lower leg support and/or from the lower leg support to the ground contact element and/or from the ground contact element to the ground. In particular, the weight of the person is additionally transmitted to the ground via the foot or shoe of the person. Preferably, the ground contact element is arranged on a rear side of the shoe of the person. When the person is sitting or partly sitting on the wearable sitting posture assisting device, the foot and/or the shoe of the person is in contact with the ground in addition to the ground contact element, Preferably, the ground contact element is arranged contactlessly with respect to the ground when the person is walking or standing while wearing the sitting posture assisting device.

In particular, the second leg unit comprises a second knee joint. The second leg unit comprises a second locking unit. The second knee joint is implemented identically to the knee joint. The second locking unit is implemented identically to the locking unit. Preferably, the locking unit is configured for locking the knee joint in different positions associated with different values of the sitting angle. Advantageously, the second locking unit is configured for locking the second knee joint in different positions associated with different values of a second sitting angle of the second knee joint. The second sitting angle is in particular defined analogously to the sitting angle. In particular, the sitting angle and the second sitting angle have an identical value in the sitting posture and/or in the partly sitting posture. It is also conceivable that the sitting angle and the second sitting angle have different values in the sitting posture and/or in the partly sitting posture.

Advantageously, the actuation element is configured for actuating the blocking element. Preferably, the actuation element is configured for enabling the person to block or unblock the blocking element. Advantageously, the actuation element is a mechanical actuation element. In particular, the actuation element is mechanically connected to the first locking unit and/or the second locking unit. It is conceivable that the actuation element is configured for controlling exactly one of the locking units. Preferably, the actuation element comprises at least one push button and/or control button and/or lever and/or slider and/or handle and/or pull handle. In particular, operation of the actuation element does not require electric power.

For the purpose of achieving a short time for locking or unlocking knee joints of a wearable sitting posture assisting device, for instance prior to sitting down and/or standing up and/or when changing a sitting angle, it is proposed that the actuation element is configured for controlling the locking unit and the second locking unit simultaneously. In particular, the knee joint and the second knee joint are lockable via the actuation element, Preferably, the actuation element is configured for triggering the locking unit and the second locking unit to lock the knee joint and the second knee joint, respectively, at different sitting angles and/or at identical sitting angles. Preferably, the person moves his legs into the desired posture, characterized by a first sitting angle value for the first sitting angle and by a second sitting angle value for the second sitting angle, which first sitting angle value and second sitting angle value may in particular be different or identical, and actuates the actuation element in order to lock the knee joint and the second knee joint according to the desired postures. It is also conceivable that the actuation unit is configured for preventing the locking unit and the second locking unit from locking the knee joint and the second knee joint, respectively, in sitting angle values which are different from each other.

In a preferred embodiment of the invention it is proposed that the actuation unit comprises at least one additional actuation element for mechanically controlling the locking unit and/or the second locking unit. Preferably, the additional actuation element is implemented identically and/or analogously to the actuation element. It is also conceivable that the actuation element and the additional actuation element are of different types. Alternatives for an implementation of the actuation element given in this disclosure are to be transferable to the additional actuation element. In particular, the actuation element and the additional actuation element are arranged at different positions. Preferably, the actuation element and the additional actuation element are arranged at different leg units of the wearable sitting posture assisting device. Advantageously, the actuation element is arranged on the first leg unit. Further advantageously, the additional actuation element is arranged on the second leg unit. Advantageously, the actuation element and/or the additional actuation element are arranged in a manner that the person can reach them with at least one hand each while wearing the wearable sitting posture assisting device, in particular when walking and/or when standing and/or when sitting down and/or when standing up and/or when partly sitting and/or when sitting. It is conceivable that the actuation element is configured for locking the knee joint and that the additional actuation element is configured for locking the second knee joint. In particular, one actuation element is assigned to one of the knee joints each. In particular in this case the knee joint and the second knee joint are lockable at different sitting angles. Furthermore, in particular in this case, it is conceivable that the actuation unit is configured for triggering locking of the first knee joint and locking of the second knee joint independently. In particular, the actuation element and the additional actuation element may be usable independently from each other. Alternatively, it is conceivable that the actuation unit is configured for preventing locking of only one of the knee joints. In particular, the actuation unit may be configured for triggering locking of the knee joint and of the second knee joint only in case of the actuation element and the additional actuation element being actuated at the same time. As a result, a possibility of a flexible and/or versatile operating logic can be achieved. Furthermore, knee joints of a wearable sitting posture assisting device can be locked and unlocked comfortably.

High flexibility concerning locking or unlocking knee joints of a wearable sitting posture assisting device in different situations, for instance when working while wearing the wearable sitting posture assisting device, can be achieved if the additional actuation element is configured for controlling the locking unit and the second locking unit simultaneously. Advantageously, the actuation element and the additional actuation element can be used alternatively and/or simultaneously used for triggering a locking of the knee joint and the second knee joint.

In a further embodiment of the invention it is proposed that the actuation element and/or the additional actuation element is mounted on the upper body wearing uni It is conceivable that the actuation element and the additional actuation element is arranged on opposite sides, preferably opposite lateral sides, of the upper body wearing unit. Preferably, the actuation element is arranged on the upper body wearing unit and the additional actuation element is arranged at the first leg unit or at second leg unit. As a result, a person wearing a wearable sitting posture assisting device is enabled to freely choose a desired actuation element for locking or unlocking knee joints.

For the purpose of achieving advantageous characteristics regarding construction and/or design, it is proposed that the actuation unit comprises at least one transmission unit, which transmission unit is configured for at least partly, in particular completely, in particular mechanically transmitting an actuation force from the actuation element and/or from the second actuation element to the locking unit and/or to the second locking unit. Advantageously, the actuation force is a force exerted onto the actuation element, preferably by the person. In particular, the actuation force may be a pushing force or a pulling force, in particular depending on whether a locking or an unlocking is requested.

For the purpose of reducing complexity of design and/or achieving a high degree of durability, it is proposed that the transmission unit is at least partly implemented as a Bowden cable. Preferably the transmission unit comprises at least one first transmission element. Further preferably, the first transmission element is implemented as the Bowden cable. Advantageously, the first transmission element is connected to the locking unit and/or to the second locking unit.

For the purpose of achieving a high degree of comfort, in particular while wearing and/or while putting on and/or off a wearable sitting posture assisting device, it is proposed that the transmission unit comprises at least one second transmission element, and at least one connection interface, which connection interface implements a detachable connection between the first transmission element and the second transmission element. Advantageously, the second transmission element is implemented as a Bowden cable. It is also conceivable that the first transmission element and/or the second transmission element are implemented as a pull cable and/or as a push rod and/or as a chain and/or as a belt or the like. In particular, the connection interface is configured for transmitting a pulling force and/or a pushing force between the first transmission element and the second transmission element. Advantageously, the detachable connection is configured for being opened and/or closed with one hand.

In a preferred embodiment of the invention, it is proposed that the connection interface comprises at least one Bowden cable connector configured for connecting and separating at least two Bowden cables. Preferably, the first transmission element comprises at least one inner cable and at least one Bowden cable housing. In particular, the inner cable is arranged within the Bowden cable housing. Preferably, the second transmission element comprises at least one inner cable and at least one Bowden cable housing, in particular analogously to the first transmission element. Advantageously, the Bowden cable connector implements a detachable connection between the inner cable of the first transmission element and the inner cable of the second transmission element. Further advantageously, the Bowden cable connector implements a detachable connection between the Bowden cable housing of the first transmission element and the Bowden cable housing of the second transmission element. Preferably, the first transmission element comprises at least one connection element for connecting to the Bowden cable connector and/or to the second transmission element. Further preferably, the second transmission element comprises at least one connection element for connecting to the Bowden cable connector and/or to the first transmission element. As a result, a high degree of mechanical strength, in particular regarding pushing and/or pulling forces, can be achieved.

For the purpose of providing a durable detachable connection between transmission elements it is proposed that the connection interface comprises at least one bayonet lock. Advantageously, the connection interface comprises at least one housing which implements the bayonet lock. Preferably, the connection element of the first transmission element and/or the connection element of the second transmission element are arranged within the housing of the connection interface in a connected state. Advantageously, the housing comprises a first housing element and a second housing element which are connectable to and disconnectable from each other. Preferably, the connection element of the first transmission element is, in particular permanently, in particular in the connected state and/or in a disconnected state, arranged within the first housing element. Further preferably, the connection element of the second transmission element is, in particular permanently, in particular in the connected state and/or in a disconnected state, arranged within the second housing element.

It is further proposed that the connection interface comprises at least one magnetic connection and/or at least one click connection, in particular between the first transmission element and the second transmission element. As a result, a person putting on or off a wearable sitting posture assisting device is enabled to easily and/or quickly connect and/or disconnect transmission elements. It is conceivable that the first transmission element is magnetically connected to the second transmission element. In particular in this case, it is conceivable that the connection element of the first transmission element and/or the connection element of the second transmission element comprises at least one magnet. It is also conceivable that the connection element of the first transmission element and/or the connection element of the second transmission element comprises at least one latching element.

For the purpose of enabling a person to put on a wearable sitting posture assisting device in different steps and/or piece by piece, it is proposed that the wearable sitting posture assisting device comprises at least one leg unit connector which implements a detachable connection between the upper body wearing unit and the leg unit and/or between the upper body wearing unit and the second leg unit. Advantageously, the leg unit connector implements a detachable connection between the upper body wearing unit and the leg unit. Preferably, the wearable sitting posture assisting device comprises a second leg unit connector which implements a detachable connection between the upper body wearing unit and the second leg unit. Preferably, the leg unit connector comprises at least one plug fastener. It is also conceivable that the leg unit connector is implemented as a magnetic connector. It is further conceivable that the leg unit connector comprises at least one socket and/or at least one plug and/or at least one lock, in particular a belt lock, and/or at least one tongue element, in particular a belt tongue.

In an advantageous embodiment of the invention, it is proposed that the connection interface is at least partly arranged within and/or integrated in the leg unit connector. In particular in this case, it is conceivable that the leg unit connector is implemented differently compared to the second leg unit connector. In particular, the second leg unit connector is configured, in particular solely, for connecting the upper body wearing unit and the second leg unit. In particular in this case, the transmission unit is preferably arranged entirely outside and/or spaced from the second leg unit connector. Advantageously, the transmission unit comprises a second connection interface, which is implemented analogously to the connection interface. Further advantageously, the second connection interface is at least partly arranged within and/or integrated in the second leg unit connector. As a result, protection against impacts and/or a simplified handling can be achieved.

Furthermore, a method for putting on the wearable sitting posture assisting device is proposed, wherein the upper body wearing unit is connected to the leg unit and/or to the second leg unit via the leg unit connector. In particular, when putting on the wearable sitting posture assisting device the person puts on the upper body wearing unit in a first method step. In a second method step, in particular subsequently to the first method step, the person in particular puts on the first leg unit and the second leg unit. Advantageously, in a third method step the person connects the upper body wearing unit to the leg unit and/or to the second leg unit via the leg unit connector. Preferably, the person puts off the wearable sitting posture assisting device in reversed order. As a result, a high degree of comfort and/or of user-friendliness, in particular during putting on or off a wearable sitting posture assisting device, is achieved. Furthermore, a person is enabled to put on the wearable sitting posture assisting device comfortably in different steps.

Herein the wearable sitting posture assisting device and the method according to the invention are not to be limited to the application and implementation described above. In particular, for the purpose of fulfilling a functionality herein described, the wearable sitting posture assisting device and the method according to the invention may comprise a number of respective elements, structural components, units and/or steps that differ from the number mentioned herein. Furthermore, regarding the value ranges mentioned in this disclosure, values within the limits mentioned are to be understood to be also disclosed and to be used as applicable.

DRAWINGS

Further advantages may become apparent from the following description of the drawing. In the drawing exemplary embodiments of the invention are shown. The drawing, the description and the claims contain a plurality of features in combination. The person having ordinary skill in the art will purposefully also consider the features separately and will find further expedient combinations.

If there is more than one specimen of a certain object, only one of these is given a reference numeral in the figures and in the description. The description of this specimen may be correspondingly transferred to the other specimens of the object.

Figure 2:
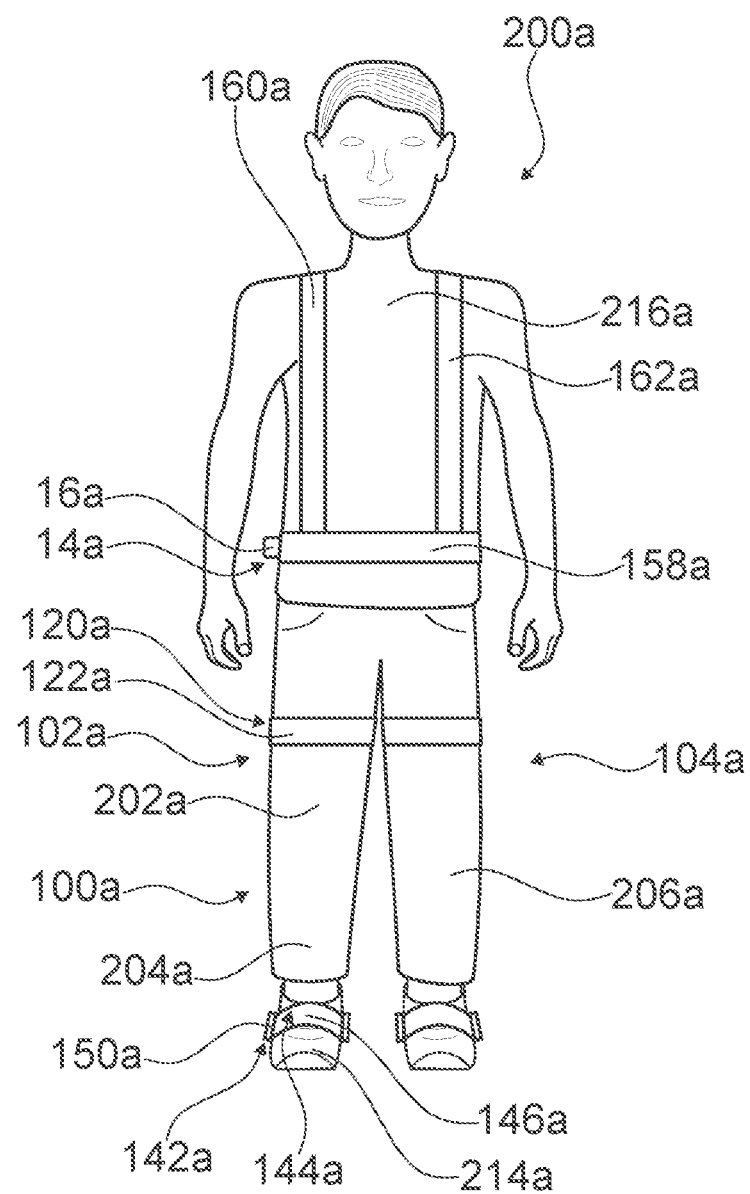
Figure 3:
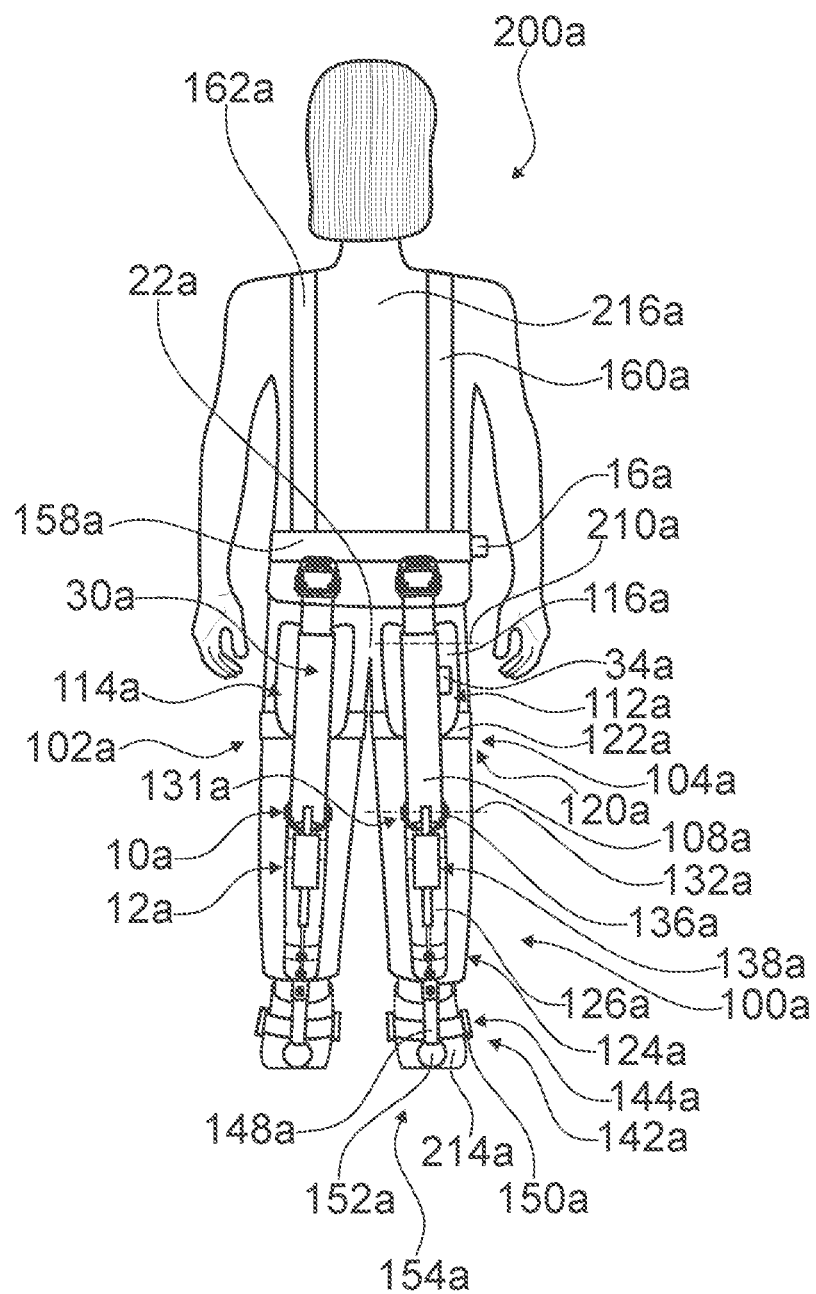
Figure 4:
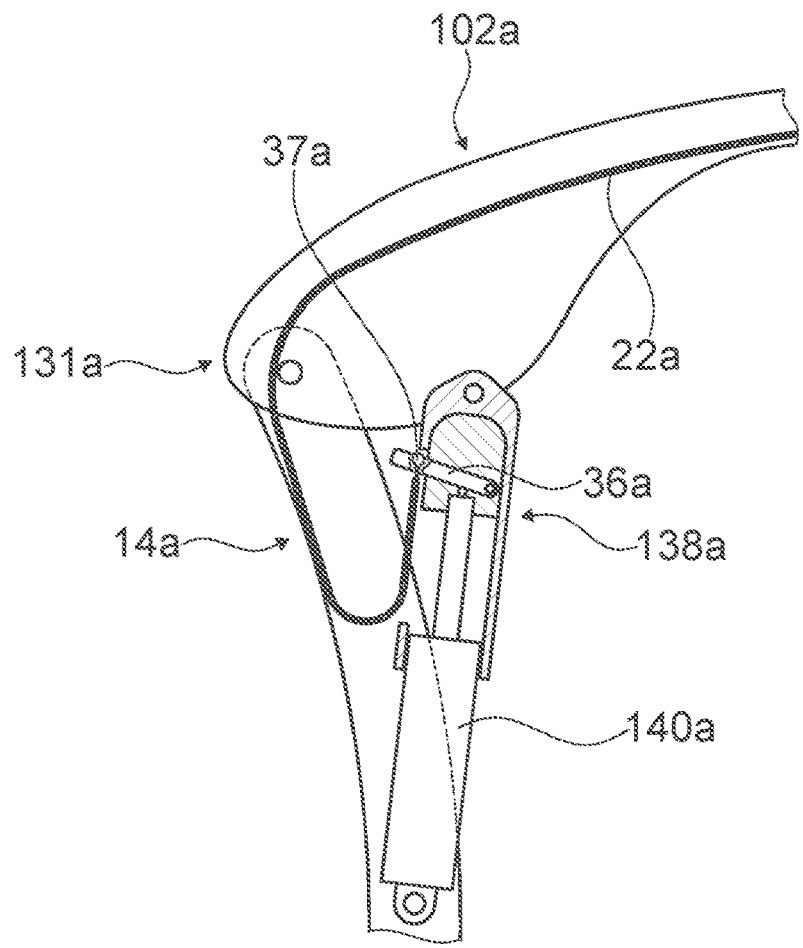
Figure 5:
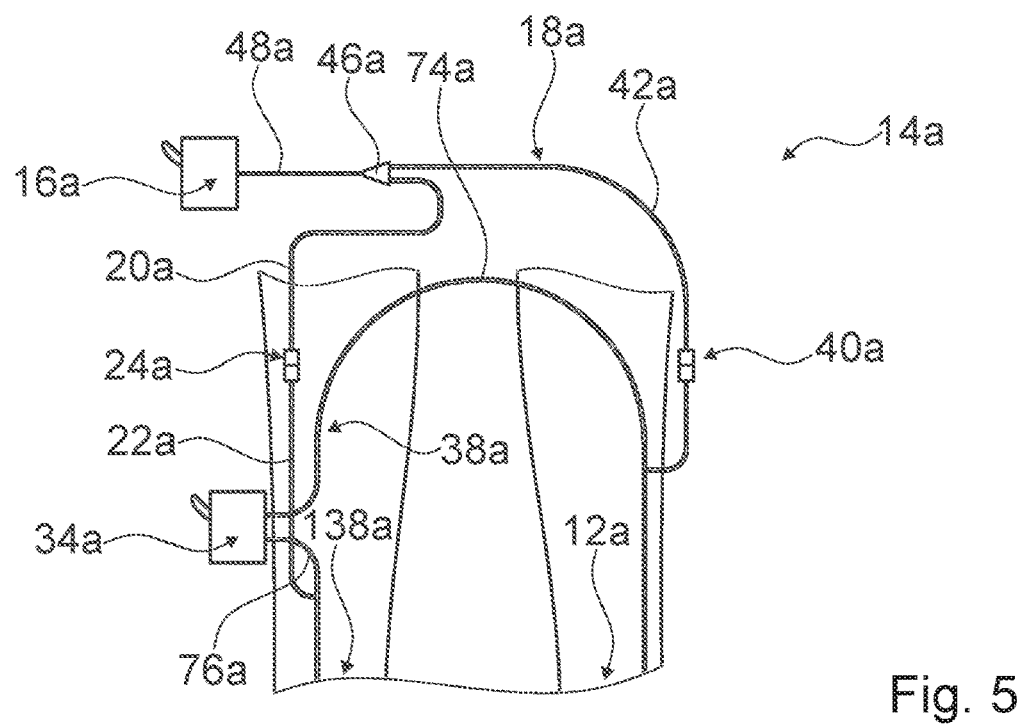
Figure 6:
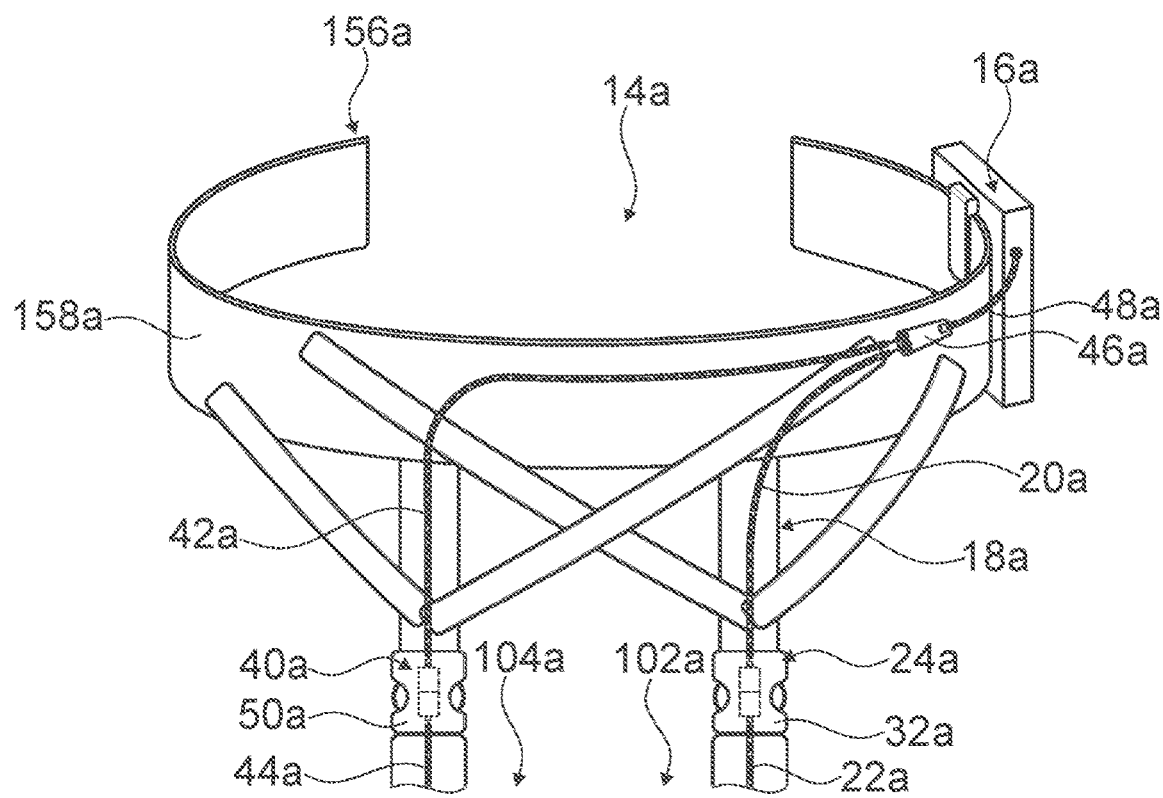
Figure 7:
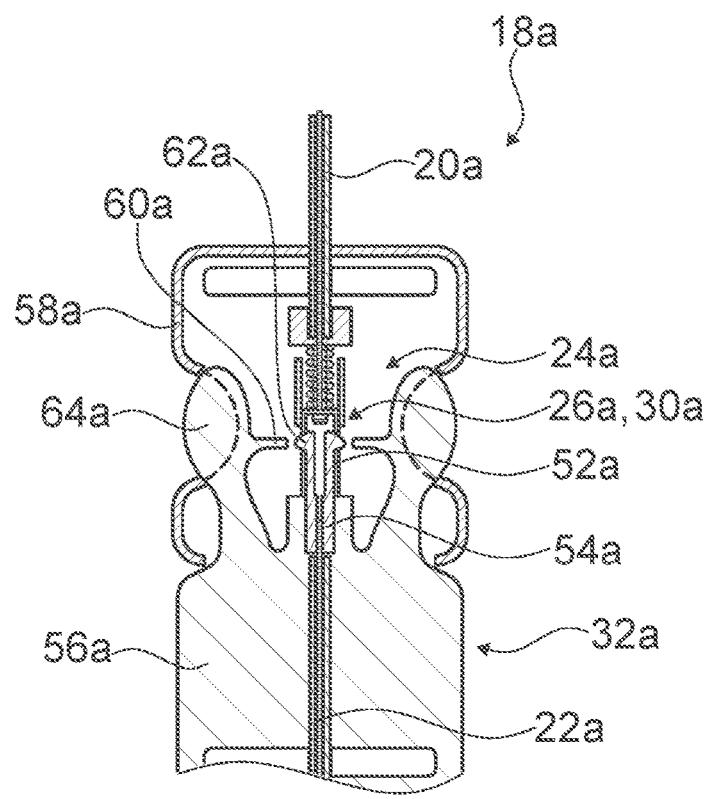
Figure 8:
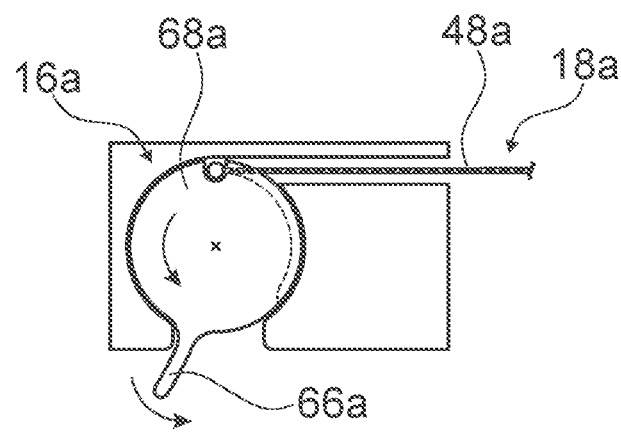
Figure 9:
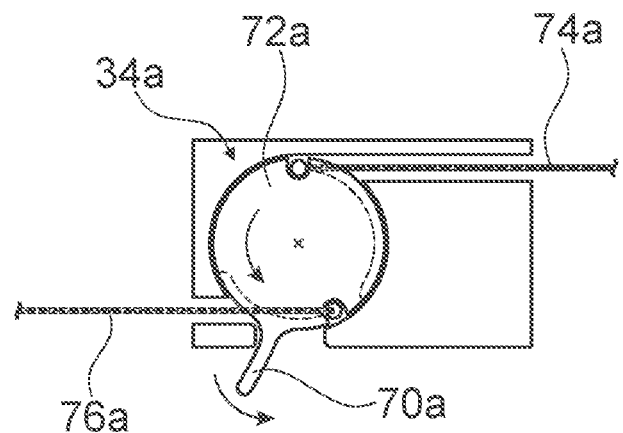
Figure 10:
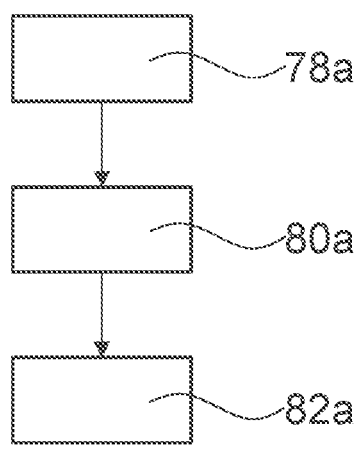
Figure 11:
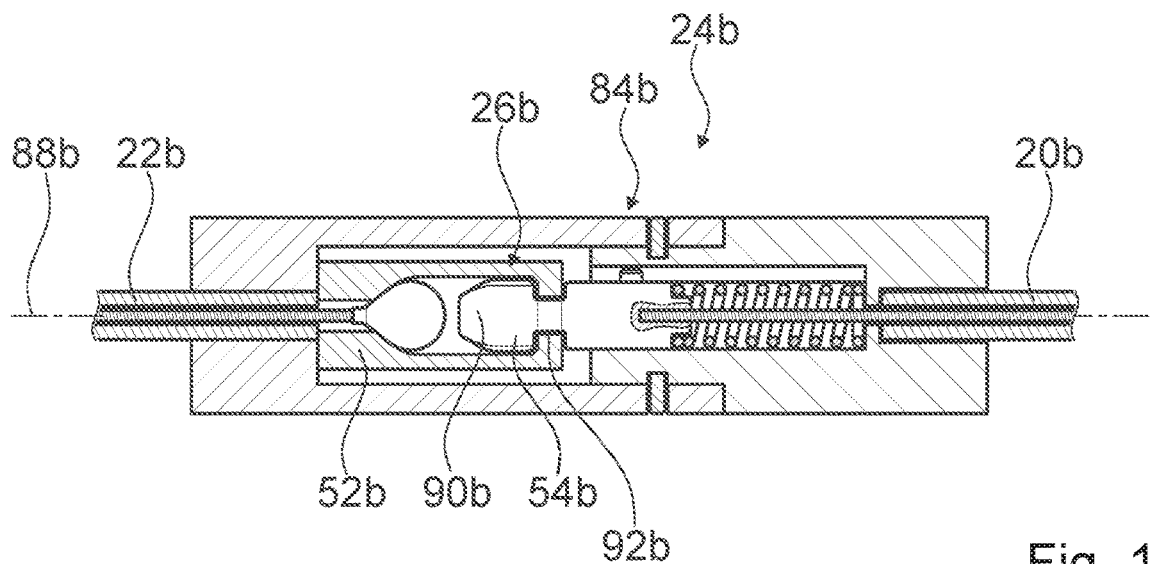
Figure 12:
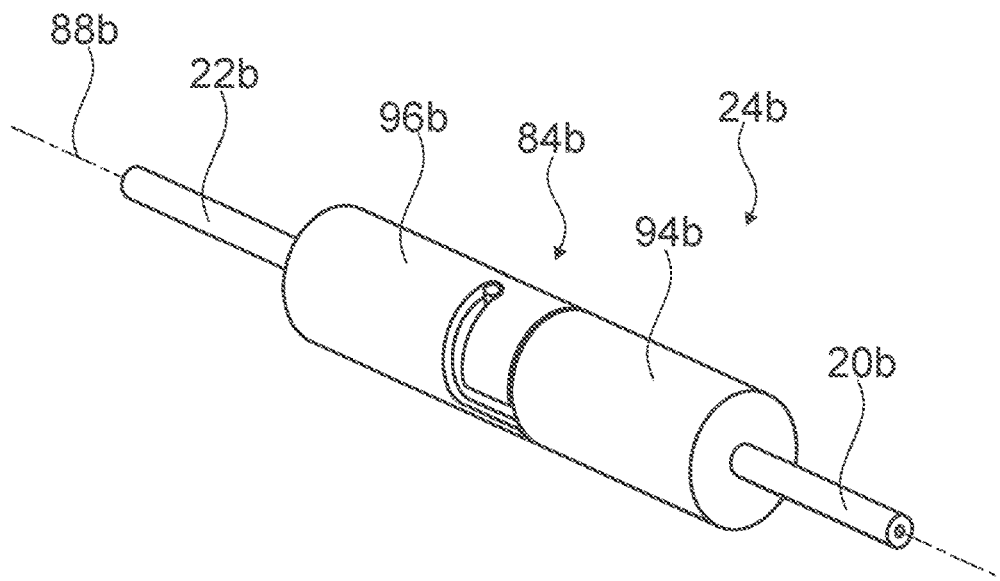
Figure 13:
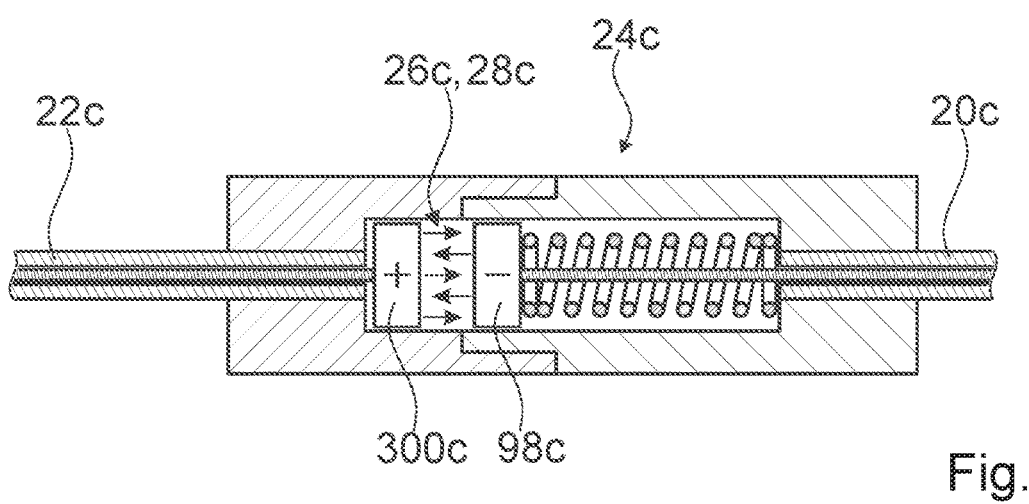
Figure 14:
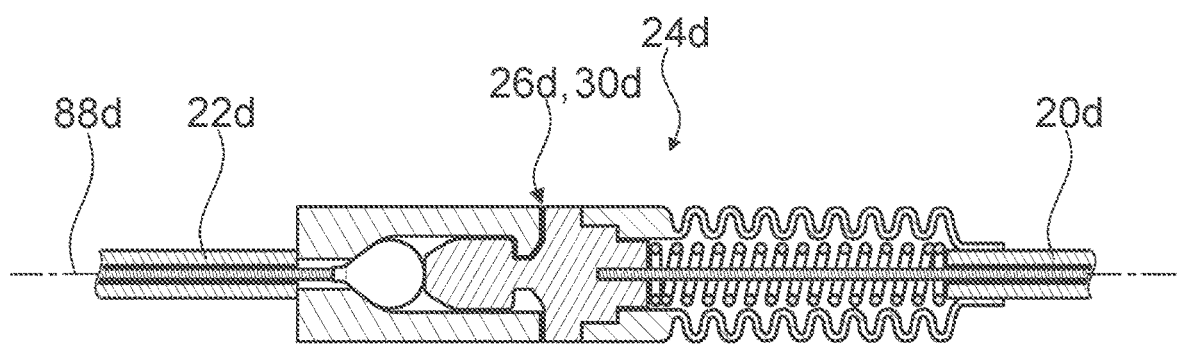
Figure 15:
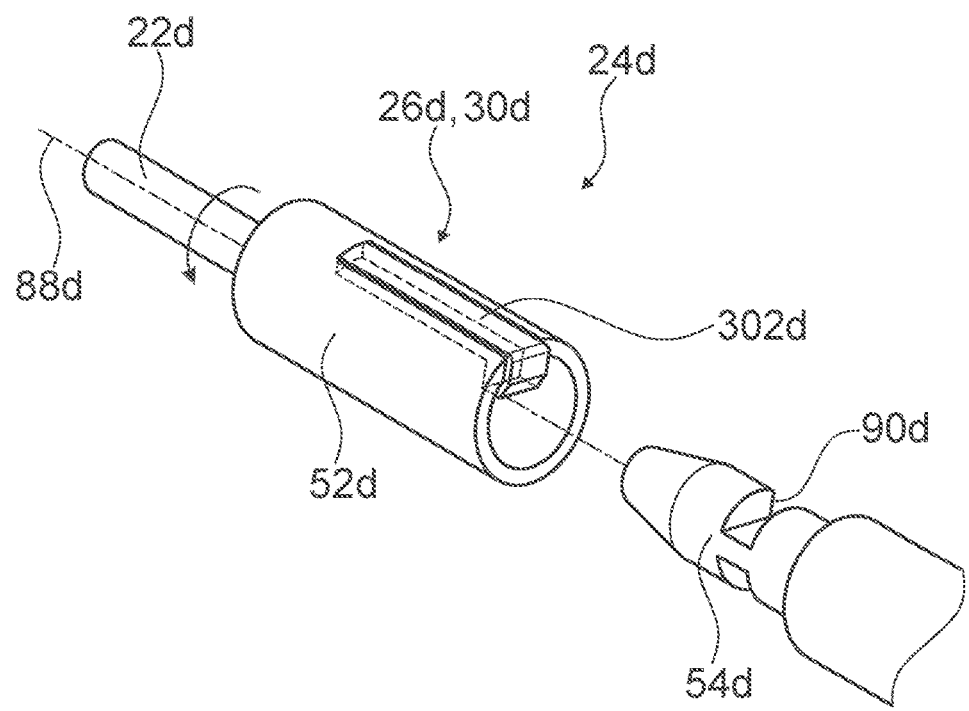
Figure 16:
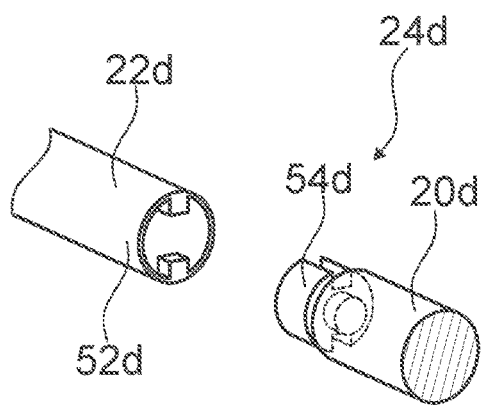
Figure 17:
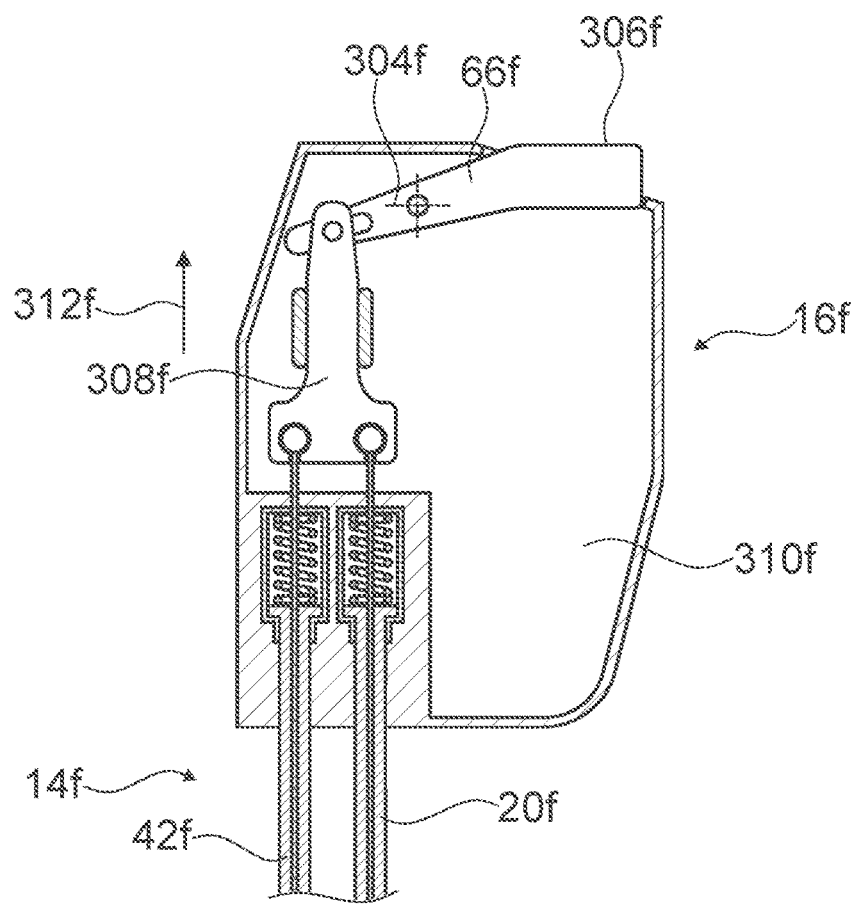
Figure 18:
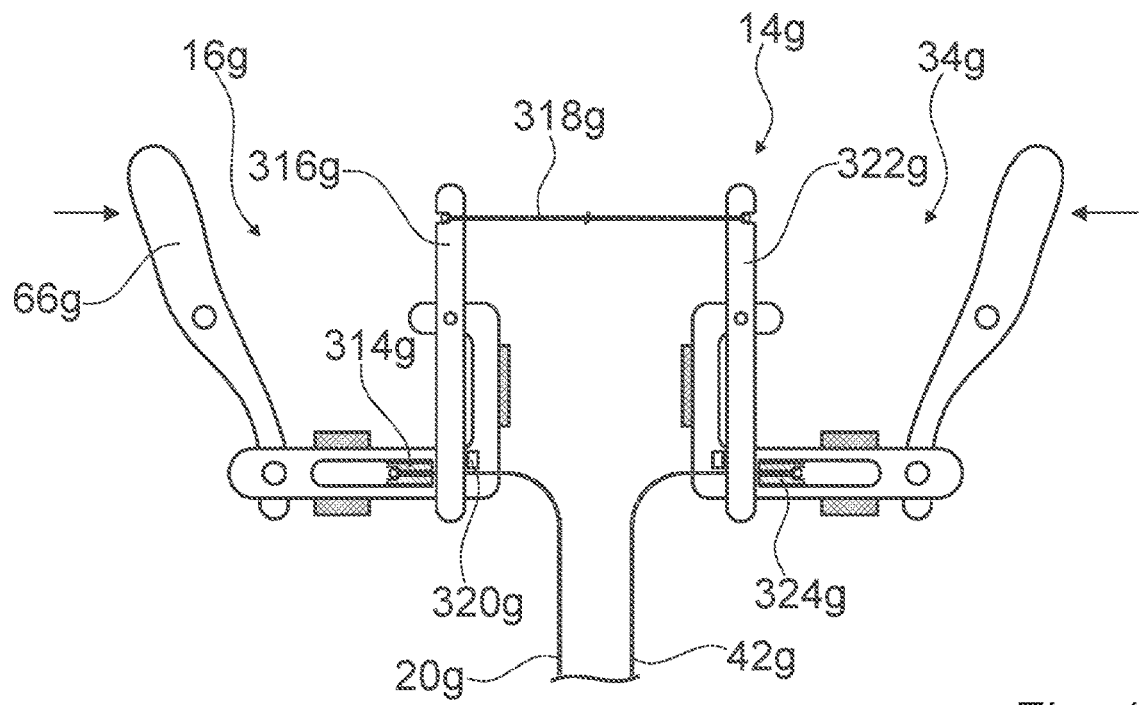
Figure 19:
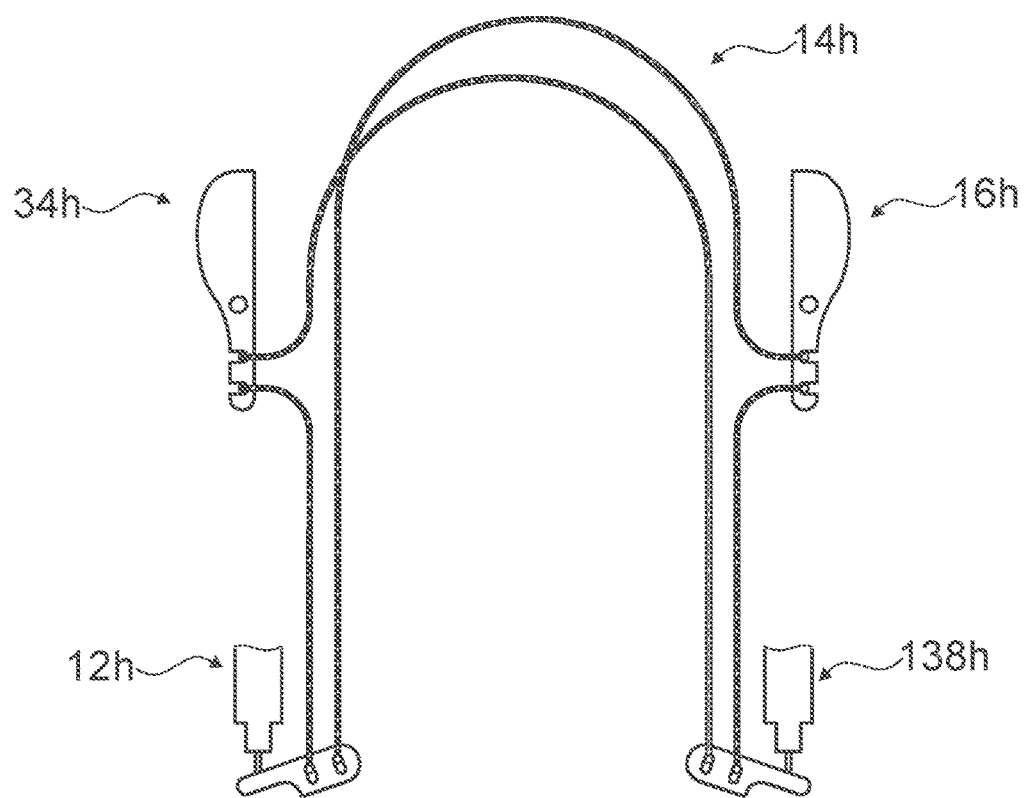
Figure 20:
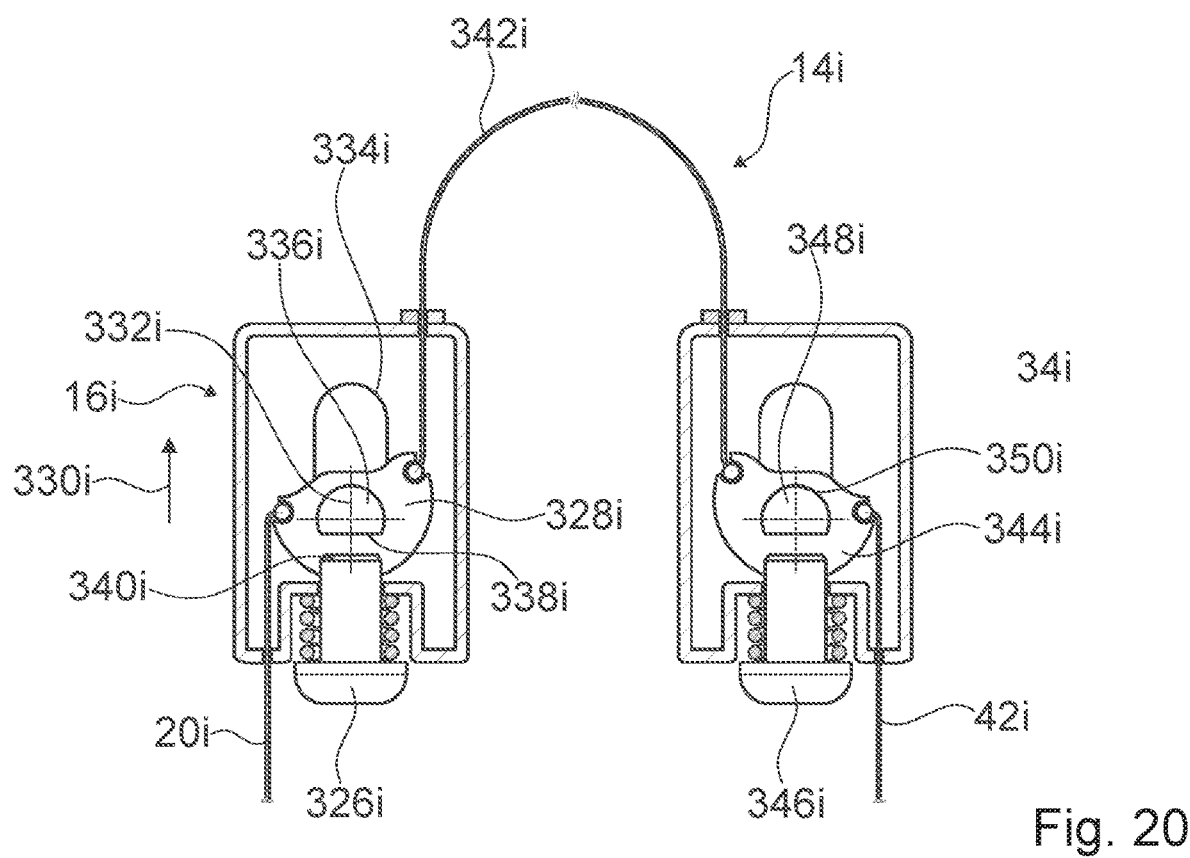
Figure 21:
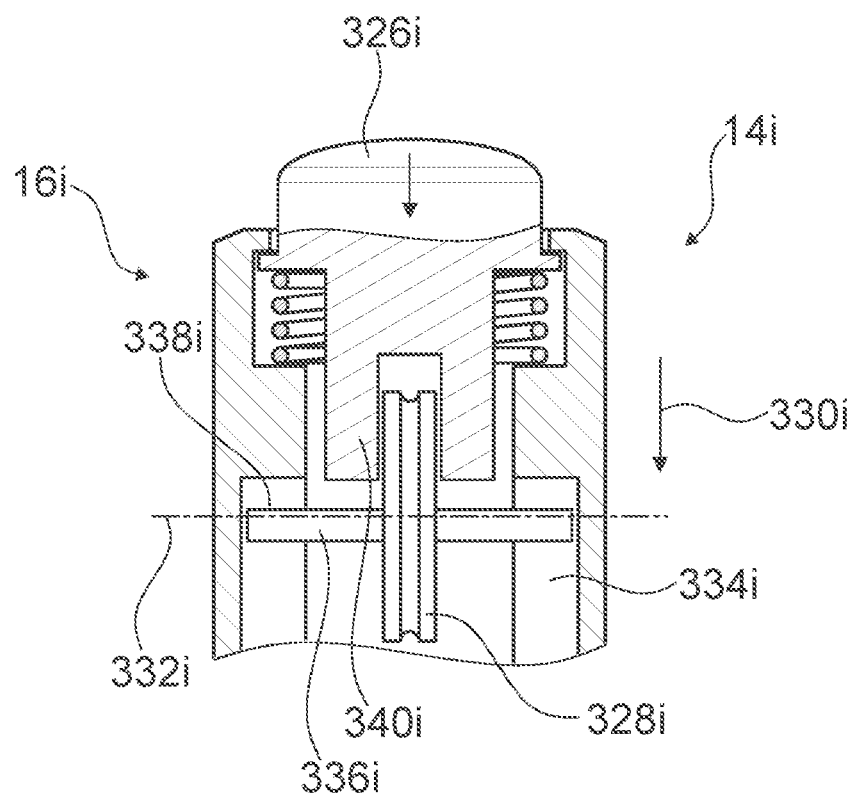
Figure 22:
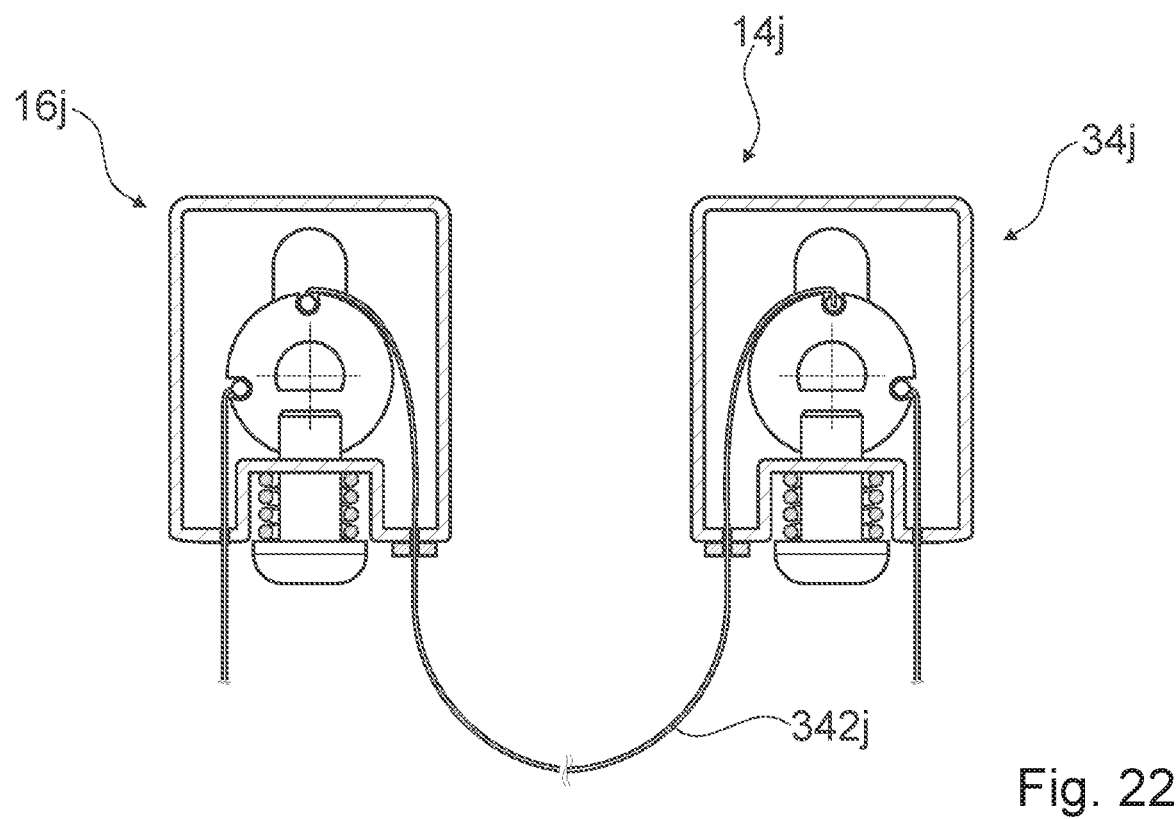

It is shown in:

FIG. 1 a person wearing a wearable sitting posture assisting device, in a schematic lateral view, FIG. 2 the person wearing the wearable sitting posture assisting device, in a schematic front view, FIG. 3 the person wearing the wearable sitting posture assisting device in a schematic rear view, FIG. 4 a portion of a leg unit of the wearable sitting posture assisting device, in a schematic sectional lateral view, FIG. 5 a portion of an actuation unit of the wearable sitting posture assisting device, in a schematic front view, FIG. 6 a portion of the actuation unit, in a schematic rear view, FIG. 7 a leg unit connector of the wearable sitting posture assisting device and a connection interface of the actuation unit, in a schematic sectional top view, FIG. 8 an actuation element of the actuation unit, in a schematic sectional view, FIG. 9 an additional actuation element of the actuation unit, in a schematic sectional view, FIG. 10 a schematic flow chart of a method for putting on the wearable sitting posture assisting device, FIG. 11 a first alternative connection interface, in a schematic sectional view, FIG. 12 the first alternative connection interface, in a perspective view, FIG. 13 a second alternative connection interface, in a schematic sectional view, FIG. 14 a third alternative connection interface, in a schematic sectional view, FIG. 15 the third alternative connection interface, in a perspective view, FIG. 16 a fourth alternative connection interface, in a perspective view, FIG. 17 a portion of a first alternative actuation unit, in a schematic sectional view, FIG. 18 a portion of a second alternative actuation unit, in a schematic view, FIG. 19 a portion of a third alternative actuation unit, in a schematic view, FIG. 20 a portion of a fourth alternative actuation unit, in a schematic sectional front view, FIG. 21 a portion of the fourth alternative actuation unit, in a schematic sectional lateral view, and FIG. 22 a portion of a fifth alternative actuation unit, in a schematic sectional view.

DESCRIPTION OF THE EXEMPLARY EMBODIMENTS

FIG. 1 shows a person 200a wearing a wearable sitting posture assisting device 100a. The wearable sitting posture assisting device 100a is configured for receiving a weight force of the person 200a in a sitting posture or in a partly sitting posture. In FIG. 1 the person 200a is shown in a partly sitting posture. In the partly sitting posture a knee 202a of the person is partly bent. In a sitting posture the knee 202a is bent more strongly than in the partly sitting posture. The wearable sitting posture assisting device 100a is configured for allowing the person 200a to sit down on it in different sitting postures and in different partly sitting postures. Furthermore, the wearable sitting posture assisting device 100a is configured for allowing the person 200a to walk while wearing the wearable sitting posture assisting device 100a. In addition, the wearable sitting posture assisting device 100a is configured for allowing the person 200a to stand and/or stand up and/or sit down and/or walk while wearing the wearable sitting posture assisting device 100a.

FIG. 2 shows the person 200a wearing the wearable sitting posture assisting device 100a, in a schematic front view. FIG. 3 shows the person 200a wearing the wearable sitting posture assisting device 100a, in a schematic rear view. In FIGS. 1 to 3 the wearable sitting posture assisting device 100a is shown in a normal wearing condition. The normal wearing conditions encompasses a condition in which the person 200a is sitting or partly sitting on the wearable sitting posture assisting device 100a, a condition in which the person 200a is standing up, a condition in which the person 200a is sitting down, a condition in which the person 200a is standing, and a condition in which the person 200a is walking, in each case while wearing the wearable sitting posture assisting device 100a. In the shown case the person 200a is wearing the wearable sitting posture assisting device 100a in a factory building, in particular while working on an assembly line. In a similar fashion it is conceivable that the person 200a wears the wearable sitting posture assisting device 100a in an office building, in a factory building, in a service building, outside, at work, at home, while working, during breaks, etc. Advantageously, the person 200a wears the wearable sitting posture assisting device 100a during an activity which requires the person 200a to sit down and/or to partly sit down and/or to stand up and/or to stand and/or to walk repeatedly. The person 200a can then sit down on the wearable sitting posture assisting device 100a when required, stand up while wearing the wearable sitting posture assisting device 100a when required, and walk while wearing the wearable sitting posture assisting device 100a when required.

The wearable sitting posture assisting device 100a comprises a leg unit 102a. Furthermore, the wearable sitting posture assisting device 100a comprises an second leg unit 104a. The second leg unit 104a is implemented identically to the leg unit 102a. Therefore, in the following, only the leg unit 102a is described in detail. The description of the leg unit 102a is to be understood as transferable to the second leg unit 104a. It is also conceivable that an second leg unit is implemented mirror-symmetrically to the leg unit. In particular, it is conceivable that a leg unit and an second leg unit are implemented as right leg unit and left leg unit, respectively, or vice versa.

In the case shown, the person 200a is wearing the leg unit 102a on a right leg 204a. The leg unit 102a is arranged on a rear side 211a of the leg 204a of the person 200a. Furthermore, the person 200a is wearing the second leg unit 104a on a left leg 206a. It is also conceivable that a person wears a leg unit on a left leg and an second leg unit on a right leg. Furthermore, it is conceivable that a person only wears one leg unit. In addition, it is conceivable that a wearable sitting posture assisting device comprises only one leg unit. It is also conceivable that a leg unit is arranged on a lateral side of a leg and/or on a front side of a leg and/or between two legs of a person.

The person 200a is sitting or partly sitting on the wearable sitting posture assisting device 100a in a sitting direction 134a. The person 200a faces and/or looks in the sitting direction 134a when facing forward. The sitting direction 134a is oriented parallel to a ground on which the person 200a is sitting or walking or standing.

The leg unit 102a comprises an upper leg 106a. The upper leg 106a comprises an upper leg support 108a. The upper leg 106a has an upper leg longitudinal axis 110a. The upper leg longitudinal axis 110a is oriented perpendicularly to the sitting direction 134a. The upper leg support 108a has a main extension direction which is oriented parallel to the upper leg longitudinal axis 110a. The upper leg longitudinal axis 110a is oriented parallel to a main extension direction of a thigh 208a of the leg 204a of the person, in particular when the person 200a is sitting, and/or partly sitting and/or walking and/or standing up and/or standing while wearing the wearable sitting posture assisting device 100a.

The upper leg 106a comprises a seat unit 112a. The seat unit 112a is connected to the upper leg support 108a. In the partly sitting posture and/or in the sitting posture the person 200a is sitting on the seat unit 112a. In the case shown the person 200a is sitting on the seat unit 112a and on a seat unit 114a of the second leg unit 104a in the partly sitting posture. The seat unit 112a comprises a sitting element 116a. The sitting element 116a contacts the thigh 208a of the person 200a. Furthermore, in the sitting posture and/or in the partly sitting posture the sitting element 116a contacts a buttock 210a of the person 200a. The seat unit 112a comprises a sitting surface 118a. The sitting element 116a comprises the sitting surface 118a. The sitting surface 118a is configured for allowing the person 200a to sit down on it with the thigh 208a and/or with the buttock 210a. A shape of the sitting surface 118a is at least partly adjusted to the thigh 208a and/or to the buttock 210a of the person 200a. The sitting surface 118a is curved. The sitting surface 118a is concavely curved and/or bent.

It is also conceivable that a wearable sitting posture assisting device comprises only one seat unit, in particular a common seat unit of two leg units. In particular, in this case it is conceivable that the seat unit is saddle-shaped and/or implemented in the manner of a saddle, in particular arranged between the legs of a person.

The upper leg 106a comprises a thigh connection unit 120a for connecting to the thigh 208a of the person 200a. The thigh connection unit 120a is connected to the upper leg support 108a. The thigh connection unit 120a is configured for connecting the upper leg 106a to the thigh 208a of the person 200a. The thigh connection unit 120a comprises a thigh strap 122a. The thigh strap 122a is fixed to the thigh 208a of the person 200a.

The wearable sitting posture assisting device 100a comprises a lower leg 124a. The lower leg 124a comprises a lower leg support 126a. The lower leg 124a has a lower leg longitudinal axis 128a. The lower leg longitudinal axis 128a is oriented perpendicularly to the sitting direction. The lower leg longitudinal axis 128a and the upper leg longitudinal axis 110a are arranged in a common plane. The lower leg support 126a has a main extension direction which is oriented parallel to the lower leg longitudinal axis 128a. The lower leg longitudinal axis 128a is oriented parallel to a main extension direction of a shank 212a of the leg 204a of the person, in particular when the person 200a is sitting, and/or partly sitting and/or walking and/or standing while wearing the wearable sitting posture assisting device 100a.

The upper leg 106a and the lower leg 124a define a sitting angle 130a. The sitting angle 130a is an angle included by the upper leg longitudinal axis 110a and the lower leg longitudinal axis 128a. The sitting angle 130a is similar or identical to an angle between the thigh 208a and the shank 212a of the person 200a. The sitting angle 130a having a value between 60° and 130°, in particular a value of approximately 90°, corresponds to different sitting postures or to at least one sitting posture. The sitting angle 130a having a value between 130° and 170° corresponds to different partly sitting postures. In case the person 200a is standing while wearing the wearable sitting posture assisting device 100a the sitting angle 130a has a value between 160° and 180°, in particular a value of approximately 180°. In case the person 200a is walking while wearing the wearable sitting posture assisting device 100a the sitting angle 130a may significantly differ from 180°, in particular in case the person 200a bends his knee 202a. In the sitting posture and/or in the partly sitting posture and/or when standing the sitting angle 130a and an analogously defined second sitting angle of the second leg unit 104a are advantageously identical. However, it is also conceivable that the person 200a is sitting on the wearable sitting posture assisting device 100a in a sitting posture or a partly sitting posture with the sitting angle 130a and the second sitting angle being differing, in particular by up to 5°, by up to 10°, by up to 15°, by up to 20°, by up to 30°, by up to 40°, or by more. When the person 200a is walking while wearing the wearable sitting posture assisting device 100a the sitting angle 130a and the second sitting angle may significantly differ, for instance in case the person bends his knees differently.

The leg unit 102a comprises a knee joint 131a which pivotably connects the upper leg 106a to the lower leg 124a. The knee joint 131a connects the upper leg 106a to the lower leg 124a pivotably about a knee joint axis 132a. The knee joint axis 132a is oriented perpendicularly with respect to the upper leg longitudinal axis 110a. The knee joint axis 132a is oriented perpendicularly to the lower leg longitudinal axis 128a. The knee joint axis 132a is oriented perpendicularly to the sitting direction 134a. The knee joint 131a is partly implemented integrally with the upper leg support 108a. The knee joint 131a is partly implemented integrally with the lower leg support 126a. The knee joint 131a comprises at least one bearing 136a which connects the upper leg support 108a to the lower leg support 126a.

The leg unit 102a comprises a locking unit 138a which is configured for locking the knee joint 131a. The locking unit 138a is configured for limiting the sitting angle 130a to a minimum value. The locking unit 138a is configured for allowing the person 200a to choose the minimum value of the sitting angle 130a. In case the locking unit 138a is in a locked state the person 200a can sit down on the wearable sitting posture assisting device 100a with the sitting angle 130a having the minimum value. The locking unit 138a is configured for being actuated by the person 200a. The locking unit 138a comprises a blocking element 140a. The blocking element 140a is a spring, in particular a gas spring. The blocking element 140a is configured for being locked at different lengths. The blocking element 140a is connected to the upper leg support 108a. The blocking element 140a is connected to the lower leg support 126a. The blocking element 140a is configured for damping a movement of the upper leg 106a with respect to the lower leg 124a, in particular when the person 200a is sitting down.

The leg unit 102a comprises a foot unit 142a. The foot unit 142a is configured for connecting to a shoe 214a and/or to a foot of the person 200a. The foot unit 142a comprises a shoe connector 144a for connecting to the shoe 214a and/or to the foot of the person 200a. The foot connector 144a comprises a strap 146a which is fixed to the shoe 214a of the person 200a. The foot unit 142a comprises a foot unit support 148a. The foot unit support 148a is connected to the lower leg 124a. The foot unit support 148a is connected to the lower leg support 126a. The foot unit support 148a comprises a bracket 150a. The shoe connector 144a is connected to the foot unit support 148a. The shoe connector 144a is connected to the bracket 150a. The strap 146a is connected to the bracket 150a.

The leg unit 102a comprises a ground contact unit 152a. The ground contact unit 152a is connected to the foot unit 142a. The ground contact unit 152a is connected to the lower leg support 126a. The ground contact unit 152a comprises a ground contact element 154a. When the person 200a is sitting or partly sitting on the wearable sitting posture assisting device 100a the ground contact unit 152a, in particular the ground contact element 154a, is in contact with the ground. The ground contact unit 152a, in particular the ground contact element 154a, is configured for transmitting a part of the weight force of the person 200a into the ground. The ground contact element 154a is rounded. The ground contact element 154a is spherical. The ground contact element 154a is made of rubber. However, other shapes and/or materials are conceivable for a ground contact element as mentioned above.

In case the person 200a is sitting or partly sitting on the wearable sitting posture assisting device 100a the weight force of the person 200a is at least partly, in particular directly or indirectly, transmitted from the seat unit 112a to the upper leg support 108a; from the upper leg support 108a to the knee joint 131a; from the knee joint 131a to the lower leg support 126a; from the lower leg support 126a to the ground contact element 154a; from the ground contact element 154a to the ground.

In particular, the weight force of the person 200a is additionally transmitted to the ground via the foot or shoe 214a of the person 200a. Preferably, the ground contact element 154a is arranged on a rear of the shoe 214a of the person 200a. When the person 200a is sitting or partly sitting on the wearable sitting posture assisting device 100a the foot and/or the shoe 214a of the person 200a is in contact with the ground in addition to the ground contact element 154a. Preferably, the ground contact element 154a is arranged contactlessly with respect to the ground when the person 200a is walking and/or standing while wearing the wearable sitting posture assisting device 100a.

The wearable sitting posture assisting device 100a comprises an upper body wearing unit 156a. The person 200a is wearing the upper body wearing unit 156a on his upper body 216a, which upper body 216a may include hips and/or a waist of the person 200a. The upper body wearing unit 156a comprises a belt 158a. Furthermore, the upper body wearing unit 156a comprises suspenders 160a, 162a. The leg unit 102a is connected to the upper body wearing unit 156a. The second leg unit 104a is connected to the upper body wearing unit 156a. It is conceivable that an upper body wearing unit comprises no belt and only suspenders, or vice versa. It is also conceivable that a wearable sitting posture assisting device is only connected to the legs and/or the feet and/or the shoes of a person wearing it.

The second leg unit 104a comprises a second knee joint 10a. The second knee joint 10a is implemented identically to the knee joint 131a. The second leg unit 104a comprises a second locking unit 12a for the second knee joint 10a. The second locking unit 12a is implemented identically to the locking unit 138a.

The wearable sitting posture assisting device 100a comprises an actuation unit 14a. The actuation unit 14a is implemented mechanically. The actuation unit 14a comprises a manually operable actuation element 16a for mechanically controlling the locking unit 138a. The actuation element 16a is configured for mechanically controlling the locking unit 138a and the second locking unit 12a. The actuation element 16a is configured for controlling the locking unit 138a and the second locking unit 12a simultaneously.

The actuation unit 14a comprises an additional actuation element 16a. The additional actuation element 16a is configured for mechanically controlling the locking unit 138a. The additional actuation element 16a is configured for mechanically controlling the second locking unit 12a. The additional actuation element 16a is configured for controlling the locking unit 138a and the second locking unit 12a simultaneously.

The actuation element 16a and the additional actuation element 34a can be used in alternative. The knee joint 131a and the second knee joint 10a can be controlled via the actuation element 16a and via the additional actuation element 34a, in particular in alternative.

The actuation element 16a is mounted to the upper body wearing unit 156a. In the case shown the actuation element 16a is connected to the belt 158a of the upper body wearing unit 156a. The additional actuation element 34a is mounted to the leg unit 102a. The additional actuation element 34a is mounted to the upper leg 106a of the leg unit 102a. The additional actuation element 34a is mounted to the upper leg support 108a of the upper leg 106a.

FIG. 4 shows a portion of the leg unit 102a, in a schematic sectional lateral view. The actuation unit 14a is configured for triggering a locking of the blocking element 140a. The actuation unit 14a comprises a lever 36a which is connected to the blocking element 140a. The lever 36a is movable into a locking position. When the lever 36a is in the locking position the blocking element 140a is blocked. The blocking element 140a is blockable at different lengths via the lever 36a in order to allow locking the knee joint 131a to different sitting angles 130a. The actuation unit 14a comprises a lever connector 37a which is configured for exerting a pulling force onto the lever 36a. The lever 36a is movable into the locking position by the pulling force.

FIG. 5 shows a portion of the actuation unit 14a, in a schematic front view. The actuation unit 14a comprises a transmission unit 18a. The transmission unit 18a is partly implemented as a Bowden cable. The transmission unit 18a is configured for at least partly transmitting an actuation force from the actuation element 16a to the locking unit 138a. The actuation force is a force exerted onto the actuation element 16a, in particular by the person 200a. The transmission unit 18a is configured for at least partly transmitting the actuation force from the actuation element 16a to the second locking unit 12a. When the person 200a exerts the actuation force onto the actuation element 16a, the actuation force is partly transmitted to the locking unit 138a and at the same time partly transferred to the second locking unit 12a. Accordingly, both the knee joint 131a and the second knee joint 10a are blocked simultaneously.

In the case shown, the actuation unit 14a comprises an additional transmission unit 38a. The additional transmission unit 38a is implemented analogously to the transmission unit 18a. The additional transmission unit 38a is configured for partly transmitting an actuation force exerted onto the additional actuation element 34a to the locking unit 138a and to the second locking unit 12a at the same time.

FIG. 6 shows a portion of the actuation unit 14a, in a schematic rear view. The transmission unit 18a comprises a first transmission element 20a and a second transmission element 22b. The first transmission element 20a is connected to the actuation element 16a. The second transmission element 22a is connected to the locking unit 138a. The second transmission element 22a is connected to the lever connector 37a.

The transmission unit 18a comprises a third transmission element 42a and a fourth transmission element 44a. The third transmission element 42a is connected to the actuation element 16a. The fourth transmission element 44a is connected to the second locking unit 12a.

In the case shown, the first transmission element 20a and the second transmission element 22b are implemented as Bowden cables. However, as mentioned above, it is conceivable that a transmission element is implemented as a pull cable, a push cable, a push rod or the like.

The actuation unit 14a comprises a connection interface 24a which implements a detachable connection between the first transmission element 20a and the second transmission element 22a. The transmission unit 18a is separable at the connection interface 24a, in particular in case of the upper body wearing unit 156a being separated from the leg unit 102a. In the case shown the transmission unit 18a comprises a second connection interface 40a. The transmission unit 18a is separable at the second connection interface 40a, in particular in case of the upper body wearing unit 156a being separated from the second leg unit 104a.

The transmission unit 18a comprises a Y-connector 46a. The transmission unit 18a comprises a fifth transmission element 48a. The Y-connector 46a connects the first transmission element 20a and the third transmission element 42a to the fifth transmission element 48a. The fifth transmission element 48a is directly connected to the actuation element 16a.

The wearable sitting posture assisting device 100a comprises a leg unit connector 32a which implements a detachable connection between the upper body wearing unit 156a and the leg unit 102a, in particular between the belt 158a and the leg unit 102a. The leg unit connector 32a is implemented as a plug fastener. When putting on the wearable sitting posture assisting device 100a the person 200a is enabled to first put on the upper body wearing unit 156a, subsequently put on the leg unit 102a, and subsequently close the leg unit connector 32a.

The wearable sitting posture assisting device 100a comprises a second leg unit connector 50a which implements a detachable connection between the upper body wearing unit 156a and the second leg unit 104a, in particular between the belt 158a and the second leg unit 104a. The second leg unit connector 50a is implemented identically to the leg unit connector 32a.

FIG. 7 shows the leg unit connector 32a and the connection interface 24a, in a schematic sectional top view. The connection interface 24a is at least partly arranged within the leg unit connector 32a. In the case shown the entire connection interface 24a is arranged within the leg unit connector 32a.

The connection interface 24a comprises a Bowden cable connector 26a configured for connecting and separating at least two Boden cables. The Bowden cable connector 26b implements a click connection 30a. In the case shown, the Bowden cable connector 26a implements a detachable connection between the first transmission element 20a and the second transmission element 22a. The first transmission element 20a is connected to a socket element 52a of the Bowden cable connector 26a. The second transmission element 22a is connected to a plug element 54a of the Bowden cable connector 26a. In a connected state the plug element 54a of the Bowden cable connector 26a is inserted in the socket element 52a of the Bowden cable connector 26a. The plug element 54a of the Bowden cable connector 26a is latched with the socket element 52a of the Bowden cable connector 26a.

The plug element 54a of the Bowden cable connector 26a is, in particular permanently connected to a plug element 56a of the leg unit connector 32a. The socket element 52a of the Bowden cable connector 26a is, in particular permanently connected to a socket element 58a of the leg unit connector 32a. The plug element 56a of the leg unit connector 32a is latched with the socket element 58a of the leg unit connector 32a.

The leg unit connector 32a is configured for actuating the connection interface 24a. The leg unit connector 32a is configured for opening the connection interface 24a and/or the Bowden cable connector 26a, in particular when the leg unit connector 32a is opened. The plug element 56a of the leg unit connector 32a comprises an actuating element 60a which is configured for actuating a latching element 62a of the plug element 54a of the Bowden cable connector 26a. The actuating element 60a is connected to a latching element 64a of the plug element 56a of the leg unit connector 32a.

FIG. 8 shows the actuation element 16a, in a schematic sectional view. The actuation element 16a comprises a lever 66a. The lever 66a is configured for receiving the actuation force. The lever 66a is connected to a rotatably mounted support element 68a. The support element 68a is connected to the fifth transmission element 48a. The support element 68a is configured for transmitting the actuation force partly to the transmission unit 18a, in particular as a pulling force. Owing to the Y-connector 46a the actuation force can be transmitted partly from the lever 66a to both the first transmission element 20a, in particular to the locking unit 138a, and to the third transmission element 42a, in particular to the second locking unit 12a.

FIG. 9 shows the additional actuation element 34a of the actuation unit. The additional actuation element 34a comprises a lever 70a. The additional actuation element 34a comprises a rotatably mounted support element 72a. A sixth transmission element 74a, which is in particular part of the additional transmission unit 38a, is connected to the support element 72a. A seventh transmission element 76a, which is in particular part of the additional transmission unit 38a, is connected to the support element 72a. The sixth transmission element 74a is configured for transmitting a part of an actuation force exerted onto the additional actuation element 34a to the locking unit 138a. The seventh transmission element 76a is configured for transmitting a part of the actuation force exerted onto the additional actuation element 34a to the additional locking unit 12a. The support element 72a is configured for partly transmitting the actuation force from the lever 70a to the sixth transmission element 74a, in particular to the locking unit 138a, and to the seventh transmission element 76a, in particular to the second locking unit 12a, simultaneously. The actuation element 16a and the additional actuation element 34a can be used in alternative for simultaneously blocking or unblocking the knee joint 131a and the second knee joint 10a.

It is conceivable that a wearable sitting posture assisting device comprises only one actuation element, which may for instance be mounted to a leg unit or an upper body wearing unit. Furthermore, a wearable sitting posture assisting device may comprise two actuation elements, which are mounted on two different leg units of the wearable sitting posture assisting device. In addition, it is conceivable that a wearable sitting posture assisting device comprises two actuation elements which are assigned to one locking unit of one leg unit of the wearable sitting posture assisting device each and/or which can be used to block knee joints of the wearable sitting posture assisting device simultaneously or independently. It is also conceivable that a connection interface is arranged at a different position. In particular, a connection interface may be used in order to implement a removable actuation element, for instance for implemented additional functionalities and/or for increasing comfort. It is conceivable that such a removable actuation element is configured for being held in a hand while wearing a wearable sitting posture assisting device and/or for being put on a table and/or on a workbench or the like.

FIG. 10 shows a schematic flow chart of a method for putting on the wearable sitting posture assisting device 100a. In a first method step 78a the person 200a puts on the upper body wearing unit 156a. In a second method step 80a the person 200a puts on the first leg unit 102a. In the case shown, the person 200a also puts on the second leg unit 104a in the second method step 80a. The leg unit connector 32a is in an open state in the first method step 78a and in the second method step 80a. In a third method step 82a the upper body wearing unit 156a is connected to the leg unit 102a via the leg unit connector 32a. Furthermore, in the third method step 82a the upper body wearing unit 156a is connected to the second leg unit 104a via the leg unit connector 32a.

FIG. 11 shows a first alternative connection interface 24b, in a schematic sectional view. FIG. 12 shows the first alternative connection interface 24b, in a perspective view. The first alternative connection interface 24b implements a detachable connection between a first transmission element 20b and a second transmission element 22b. The first alternative connection interface 24b comprises a bayonet lock 84b. The first alternative connection interface 24b comprises a Bowden cable connector 26b. The Bowden cable connector 26b comprises a plug element 54b and a socket element 52b. In FIG. 11 the plug element 54b is shown in a locked state. The plug element 54b can be turned about a rotation axis 88b with respect to the socket element 52b. The rotation axis 88b is oriented parallel to a main extension direction of the first transmission element 20a and the second transmission element 22a in an area of the first alternative connection interface 24b. The plug element 54b is removable from the socket element 52b in a turned state, in particular when turned by approximately 90°. The plug element 54b comprises a flattened area 90b which fits through a socket opening 92b of the socket element 52b in the turned state.

The bayonet lock 84b comprises a first bayonet lock element 94b and a second bayonet element 96b. For opening and closing the bayonet lock 84b the first bayonet lock element 94b is configured for being turned about the rotation axis 88b with respect to the second bayonet lock element 96b. The plug element 54b is turned about the rotation axis 88b when turning the first bayonet lock element 94b about the rotation axis 88b. The first alternative connection interface 24b is configured for being actuated, in particular for being opened or closed, when the bayonet lock 84a is actuated, in particular opened or closed. The bayonet lock 84b implements a housing for the Bowden cable connector 26b.

FIG. 13 shows a second alternative connection interface 24c, in a schematic sectional view. The second alternative connection interface 24c implements a detachable connection between a first transmission element 20c and a second transmission element 22c. The second alternative connection interface 24c comprises a Bowden cable connector 26c.

The second alternative connection interface 24c comprises a magnetic connection 28c. The magnetic connection 28c implements the Bowden cable connector 26c. The first transmission element 20c comprises a first magnetic connection element 98c. The second transmission element 22c comprises a second magnetic connection element 300c. The first magnetic connection element 98c is connected to the second magnetic connection element 300c in a connected state. The first magnetic connection element 98c and the second magnetic connection element 300c implement the magnetic connection 28c. It is conceivable that a magnetic connection comprises at least one electromagnet. It is also conceivable that one connection element is magnetic and one connection element is ferromagnetic.

FIG. 14 shows a third alternative connection interface 24d, in a schematic sectional view. FIG. 15 shows the third alternative connection interface 24d, in a perspective view. The third alternative connection interface 24d implements a detachable connection between a first transmission element 20d and a second transmission element 22d. The third alternative connection interface 24d comprises a Bowden cable connector 26d. The connection interface 24d comprises a click connection 30d. The Bowden cable connector 26d implements the click connection 30d.

The click connection 30d comprises a latching element 302d. The latching element 302d is part of a socket element 52d of the Bowden cable connector 26d. The click connection 30d comprises a plug element 54d. The plug element 54d is part of the Bowden cable connector 26d. The plug element 54d latches with the latching element 302d in a connected state. The plug element 54d is turnable about a rotation axis 88d with respect to the socket element 52d. The plug element 28d comprises a flattened area 90a. In a turned state the plug element 54d is removable from the socket element 52d. In the turned state the flattened area 90a can be passed past the latching element 302d out of the socket element 52d.

FIG. 16 shows a fourth alternative connection interface 24e, in a perspective view. The fourth alternative connection interface 24e implements a detachable connection between a first transmission element 20e and a second transmission element 22e. In the case shown, the first transmission element 20e and the second transmission element 22e are implemented as flexible push-pull-rods. The connection interface 24e comprises a socket element 52e and a plug element 54e. The plug element 54e and the socket element 52e are implemented in a key-lock manner. The plug element 54e is insertable into the socket element 52e. The plug element 54e is turnable about a rotation axis 88e with respect to the socket element 52e for closing a connection between the plug element 54e and the socket element 52e. In the case shown the first transmission element 20e implements the plug element 54d. Furthermore, in the case shown the second transmission element 22e implements the socket element 52e.

A connection interface comprising a plug element and a socket element implemented analogously to the plug element 54e and the socket element 52e as shown in FIG. 16, in particular with respect to their geometry, may also be used for connecting two Bowden cables.

FIG. 17 shows a portion of a first alternative actuation unit 14f, in a schematic sectional view. The first alternative actuation unit 14f comprises an actuation element 16f. The actuation element 16f comprises a lever 66f. The lever 66f is rotatably mounted to a housing 310f of the first alternative actuation element 16f. about a rotation axis 304f. The lever 66f implements a control button 306f. The lever 66f is connected to a support element 308f. The support element 308f is slidably mounted to the housing 310f. The support element 308f is movable in a direction 312f perpendicular to the rotation axis 304f.

The lever 66f is implemented to convert a pushing actuation force exerted onto the push button into a pulling force acting onto the support element 308f. The actuation unit 14f comprises two transmission elements 20f, 42f. The transmission element 30f, 42f are connected to the support element 308f. The control button 306f is configured for controlling the two transmission elements 20f, 42f simultaneously.

FIG. 18 shows a portion of a second alternative actuation unit 14g, in a schematic view. The second alternative actuation unit 14g comprises an actuation element 16g and an additional actuation element 34g. The actuation element 16g and the additional actuation element 34g are implemented for simultaneously controlling a blocking of two locking units which are not shown in FIG. 18. The locking units are controlled via a first transmission element 20g and a second transmission element 42g.

The actuation element 16g comprises a lever 66g. The lever 66g is configured for generating a pulling force on a slide element 314g. The first transmission element 20g is connected to the slide element 314g.

The actuation element 16g comprises a lever element 316g. The lever element 316g is connected to a third transmission element 318g. When the lever 66g is pulled, a stop element 320g exerts a pushing force onto the lever element 316g and the lever element 316g exerts a pulling force onto the third transmission element 318g.

The second actuation element 34g is implemented symmetrically with respect to the actuation element 16g. The second actuation element 34g is implemented identically to the actuation element 16g. The second actuation element 34g comprises a second lever element 322g. The second lever element 322g is rotatably mounted. The second lever element 322g is connected to the third transmission element 318g. When a pulling force is exerted onto the second lever element 322g by the third transmission element 318g the second lever element 322g is pushed against a second slide element 324g. The second slide element 324g then exerts a pulling force onto the second transmission element 42g. Therefore, the second actuation element 34g transmits a pulling force onto the second transmission element 42g when the actuation element 16g is actuated.

In an analogous manner the actuation element 16g transmits a pulling force onto the first transmission element 20g when the second actuation element 34g is actuated.

FIG. 19 shows a portion of a third alternative actuation unit 14h, in a schematic view. The third alternative actuation unit 14h comprises an actuation element 16h and an additional actuation element 34h. The actuation element 16h and the additional actuation element 34h are configured for mechanically controlling a locking unit 138h and a second locking unit 12h of a wearable sitting posture assisting device which is not shown in FIG. 19. Both actuation elements 16h, 34h are connected to both locking units 12h, 138h. The actuation elements 16h, 34h are configured for simultaneously blocking the locking units 12h, 138h. The actuation unit 14h is configured for requiring both actuation elements 16h, 34h to be actuated for blocking the locking units 12h, 138h.

FIG. 20 shows a portion of a fourth alternative actuation unit 14i, in a schematic sectional front view. FIG. 21 shows a portion of the fourth alternative actuation unit 14i, in a schematic sectional lateral view. The fourth alternative actuation unit 14i comprises an actuation element 16i and an additional actuation element 34i. The actuation element 16i and the additional actuation element 34i are usable in alternative for simultaneously blocking two locking units, which locking units are not shown in FIGS. 20 and 21. The additional actuation element 34i is implemented symmetrically with respect to the actuation element 16i. The additional actuation element 34i is implemented identically to the actuation element 16i. The actuation element 16i is connected to a first of the two locking units via a first transmission element 20i. The additional actuation element 34i is connected to a second of the two locking units via a second transmission element 42i.

The actuation element 16i comprises a push button 326i. The push button 326i defines a pushing direction 330i. The actuation element 16i comprises a support element 328i. In FIG. 21 the support element 328i is shown non-sectioned. The support element 328i is rotatable about a rotation axis 332i which is oriented perpendicularly to the pushing direction 330i. In FIGS. 20 and 21 the support element 328i is shown in a basic position. The support element 328i is rotatable about the rotation axis 332i in the basic position. The support element 328i is slidable in the pushing direction 330i. The actuation element 16i comprises a guiding element 334i which slidably guides the support element 328i. The guiding element 334i is implemented as a guiding slot.

The support element 328i comprises a bolt element 336i which partly is arranged rotatably and slidably within the guiding element 334i. The bolt element 336i comprises a flattened surface 338i which is oriented perpendicularly to the pushing direction 330i and parallel to the rotation axis 332i. In case of the push button 326i being pushed in the pushing direction 330i, a stop surface 340i of the push button 326i comes in contact with the flattened surface 338i. In case of the stop surface 340i being pushed against the flattened surface 338i, the support element 328i is no longer rotatable.

The first transmission element 20i is connected to the support element 328i. Pushing the push button 326i in the pushing direction 330i results in a pulling force exerted onto the first transmission element 20i, in particular since the support element 328i is non-rotatable while the push button 326i is being pushed.

The actuation unit 14i comprises a third transmission element 342i. The third transmission element 342i is implemented as a push cable. The third transmission element 342i is connected to the support element 328i. In case of the push button 326i being pushed, the third transmission element 342i transmits a pushing force to a second support element 344i of the additional actuation element 34i. The second transmission element 42i is connected to the second support element 344i. In case of a second push button 346i of the additional actuation element 34i not being pushed, the second support element 344i is rotatable about a second rotation axis 350i defined by a second bolt element 348i of the second support element 344i. The pushing force transmitted by the third transmission element 342i rotates the second support element 344i about the second rotation axis 350i. Rotation of the second support element 344i results in a pulling force exerted onto the second transmission element 42i.

In an analogous manner a pulling force is exerted onto the first transmission element 20i in case of the second push button 346i being pushed.

FIG. 22 shows a portion of a fifth alternative actuation unit 14j, in a schematic sectional view. The fifth alternative actuation unit 14j comprises an actuation element 16j and an additional actuation element 34j. The fifth alternative actuation unit 14j is implemented analogously to the fourth alternative actuation unit 14i. However, a third transmission element 342j of the fifth alternative actuation unit 14j is implemented as a pull cable instead.

The invention claimed is:

1. A wearable sitting posture assisting device for receiving a weight force of a person in a sitting posture or in a partly sitting posture and transmitting the weight force to a ground, comprising:
at least one leg unit including at least one knee joint and at least one locking unit for the knee joint;
at least one second leg unit including at least one second knee joint and at least one second locking unit; and
at least one actuation unit including at least one manually operable actuation element for mechanically controlling the locking unit and/or the second locking unit,
wherein the actuation unit comprises at least one transmission unit, which is configured for at least partly transmitting an actuation force from the actuation element to the locking unit and/or to the second locking unit, the transmission unit being at least partly implemented as a Bowden cable, and
wherein the leg unit comprises at least one upper leg and at least one lower leg, the knee joint pivotably connecting the lower leg to the upper leg, the upper leg and the lower leg together defining a sitting angle, the locking unit being configured to lock the knee joint in different positions associated with different values of the sitting angle, the sitting angle in the sitting posture being no greater than 170°.

2. The wearable sitting posture assisting device according to claim 1, wherein the actuation element is configured for controlling the locking unit and the second locking unit simultaneously.

3. The wearable sitting posture assisting device according to claim 1, wherein the transmission unit comprises at least one first transmission element, at least one second transmission element, and at least one connection interface, which connection interface implements a detachable connection between the first transmission element and the second transmission element.

4. The wearable sitting posture assisting device according to claim 3, wherein the connection interface comprises at least one Bowden cable connector configured for connecting and separating at least two Bowden cables.

5. The wearable sitting posture assisting device according to claim 3, wherein the connection interface comprises at least one bayonet lock.

6. The wearable sitting posture assisting device according to claim 3, wherein the connection interface comprises at least one magnetic connection and/or at least one click connection.

7. The wearable sitting posture assisting device according to claim 3, further comprising at least one upper body wearing unit and at least one leg unit connector which implements a detachable connection between the upper body wearing unit and the leg unit and/or between the upper body wearing unit and the second leg unit, wherein the connection interface is at least partly arranged within the leg unit connector.

8. The wearable sitting posture assisting device according to claim 1, further comprising at least one upper body wearing unit and at least one leg unit connector which implements a detachable connection between the upper body wearing unit and the leg unit and/or between the upper body wearing unit and the second leg unit.

9. The wearable sitting posture assisting device according to claim 1, wherein the actuation unit comprises at least one additional actuation element for mechanically controlling the locking unit and/or the second locking unit.

10. The wearable sitting posture assisting device according to claim 9, wherein the additional actuation element is configured for controlling the locking unit and the second locking unit simultaneously.

11. The wearable sitting posture assisting device according to claim 9, wherein the actuation element and the additional actuation element are usable in alternative for controlling the locking unit and/or the second locking unit.

12. The wearable sitting posture assisting device according to claim 1, wherein the actuation element is arranged spatially apart from the leg unit.

13. The wearable sitting posture assisting device according to claim 1, wherein the sitting angle in the sitting posture is no greater than 160°.

14. The wearable sitting posture assisting device according to claim 1, wherein the sitting angle in the sitting posture is no smaller than 60°.

15. A wearable sitting posture assisting device according to claim 1, wherein
the upper leg has an upper leg longitudinal axis,
the lower leg has a lower leg longitudinal axis, and
the sitting angle is an angle included between the upper leg longitudinal axis and the lower leg longitudinal axis on a rear side of the upper leg and the lower leg.

16. A method for putting on a wearable sitting posture assisting device for receiving a weight force of a person in a sitting posture or in a partly sitting posture and transmitting the weight force to a ground, comprising:
providing at least one leg unit that includes at least one knee joint and at least one locking unit for the knee joint, at least one second leg unit that includes at least one second knee joint and at least one second locking unit, at least one actuation unit that includes at least one manually operable actuation element for mechanically controlling the locking unit and/or the second locking unit, wherein the actuation unit comprises at least one transmission unit, which is configured for at least partly transmitting an actuation force from the actuation element to the locking unit and/or to the second locking unit, wherein the transmission unit is at least partly implemented as a Bowden cable, wherein the leg unit comprises at least one upper leg and at least one lower leg, wherein the knee joint is pivotably connecting the lower leg to the upper leg, wherein the upper leg and the lower leg together define a sitting angle, wherein the locking unit is configured to lock the knee joint in different positions associated with different values of the sitting angle, wherein in the sitting posture the sitting angle is no greater than 170°; and
putting on the first leg unit and the second leg unit.

* * * * *